United States Patent
Kira et al.

(10) Patent No.: US 7,200,254 B2
(45) Date of Patent: Apr. 3, 2007

(54) PROBE REACTIVE CHIP, SAMPLE ANALYSIS APPARATUS, AND METHOD THEREOF

(75) Inventors: Shigeki Kira, Kasugai (JP); Kazunari Yamada, Nagoya (JP); Toshikazu Hirota, Nagoya (JP); Yasuko Yoshida, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 480 days.

(21) Appl. No.: 10/235,999

(22) Filed: Sep. 5, 2002

(65) Prior Publication Data

US 2003/0152256 A1    Aug. 14, 2003

Related U.S. Application Data

(63) Continuation-in-part of application No. 10/115,864, filed on Apr. 3, 2002, now abandoned.

(30) Foreign Application Priority Data

Feb. 14, 2002    (JP)   ............................ P2002-037418

(51) Int. Cl.
     *G06K 9/00*      (2006.01)
     *G06K 9/32*      (2006.01)

(52) U.S. Cl. ...................... 382/129; 382/128; 382/151; 382/294

(58) Field of Classification Search ................ 382/128, 382/129, 294, 141, 151; 128/922; 356/39; 377/10; 435/6; 536/23.1
See application file for complete search history.

(56) References Cited

U.S. PATENT DOCUMENTS

| | | | |
|---|---|---|---|
| 5,994,076 A | 11/1999 | Chenchik et al. | ............... 435/6 |
| 6,027,880 A | 2/2000 | Cronin et al. | |
| 6,077,673 A | 6/2000 | Chenchik et al. | ............... 435/6 |
| 6,352,829 B1 | 3/2002 | Chenchik et al. | ............... 435/6 |
| 6,489,455 B2 | 12/2002 | Chenchik et al. | ........... 536/23.1 |
| 6,706,479 B2* | 3/2004 | Saraf et al. | ..................... 435/6 |
| 6,800,765 B2* | 10/2004 | Diwu et al. | .................. 549/223 |
| 2002/0042070 A1* | 4/2002 | Saraf et al. | ..................... 435/6 |
| 2002/0115072 A1 | 8/2002 | Okamoto et al. | ............... 435/6 |
| 2003/0068668 A1* | 4/2003 | Diwu et al. | ................. 435/40.5 |
| 2003/0137557 A1* | 7/2003 | Nakamura | .................... 347/44 |
| 2003/0142167 A1* | 7/2003 | Nakamura et al. | ............ 347/37 |

(Continued)

FOREIGN PATENT DOCUMENTS

JP      2000-270896      10/2000

(Continued)

*Primary Examiner*—Duy M. Dang
(74) *Attorney, Agent, or Firm*—Burr & Brown

(57) ABSTRACT

Technology is disclosed for highly accurate automated execution of processing for alignment of a detection area to a DNA microarray image file and processing for quantitative determination of success/failure of the alignment during DNA microarray analysis. A probe reactive chip used for the technology comprises a substrate; a spot region wherein spots for fixing a probe capable of specifically reacting to a sample marked so as to be optically detectable are formed in a matrix on a surface of the substrate; and a reference pattern area, which is arranged within the spot region or approximate to the spot region, and comprises a plurality of different alignment marks in order to correct misalignment of the spot during analysis of the sample on the surface of the substrate.

43 Claims, 26 Drawing Sheets

U.S. PATENT DOCUMENTS

| | | | |
|---|---|---|---|
| 2003/0152255 A1* | 8/2003 | Kira et al. | 382/129 |
| 2003/0184613 A1* | 10/2003 | Nakamura et al. | 347/40 |
| 2003/0198952 A9 | 10/2003 | Okamoto et al. | 435/6 |
| 2004/0051767 A1* | 3/2004 | Takano | 347/94 |
| 2004/0183851 A1* | 9/2004 | Nakamura | 347/20 |
| 2005/0099453 A1* | 5/2005 | Nakamura | 347/40 |

FOREIGN PATENT DOCUMENTS

| | | |
|---|---|---|
| JP | 2001-004626 | 1/2001 |
| JP | 2001-349835 | 12/2001 |
| JP | 2002-504812 | 2/2002 |
| JP | 2003-021639 | 1/2003 |
| WO | WO 99/08233 A1 | 2/1999 |
| WO | WO 00/47996 A2 | 8/2000 |
| WO | WO 01/35099 A1 | 5/2001 |
| WO | WO 02/072889 A2 | 9/2002 |
| WO | WO 03/030620 A2 | 4/2003 |

* cited by examiner

| BLOCK NO. | SPOT NO. | Cy5 | Cy3 |
|---|---|---|---|
| 1 | 1 | 1000 | 1000 |
| 1 | 2 | 200 | 200 |
| 1 | 3 | 2000 | 2000 |
| ⋮ | ⋮ | ⋮ | ⋮ |

FIG.27
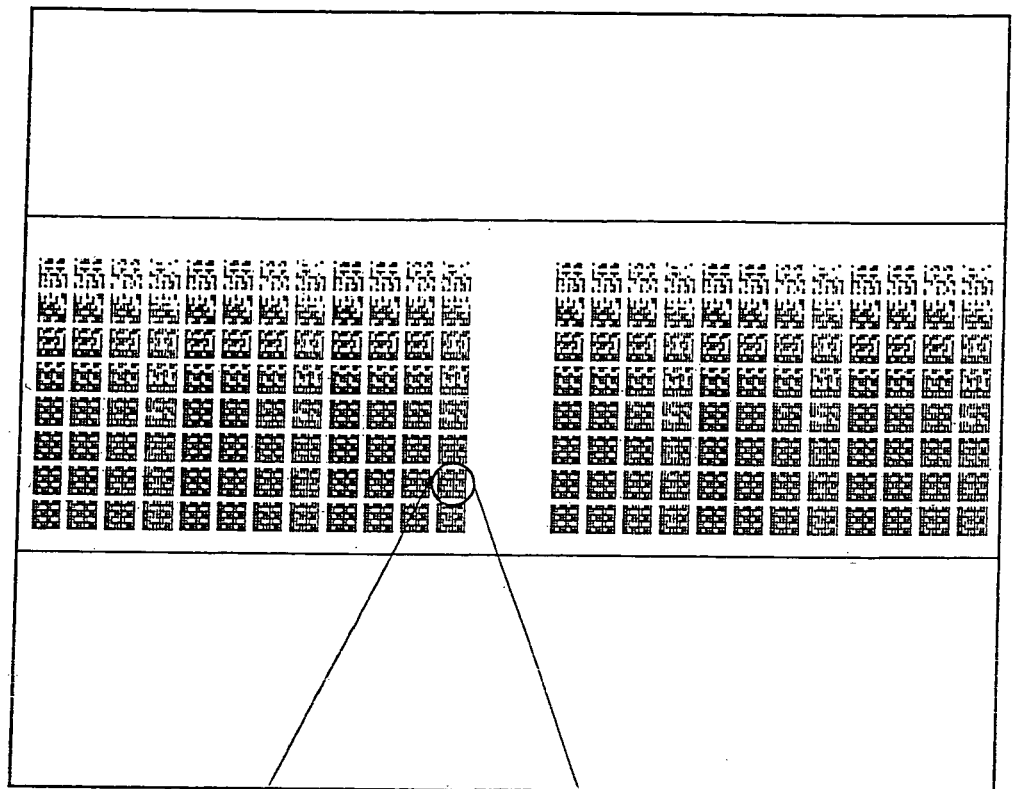
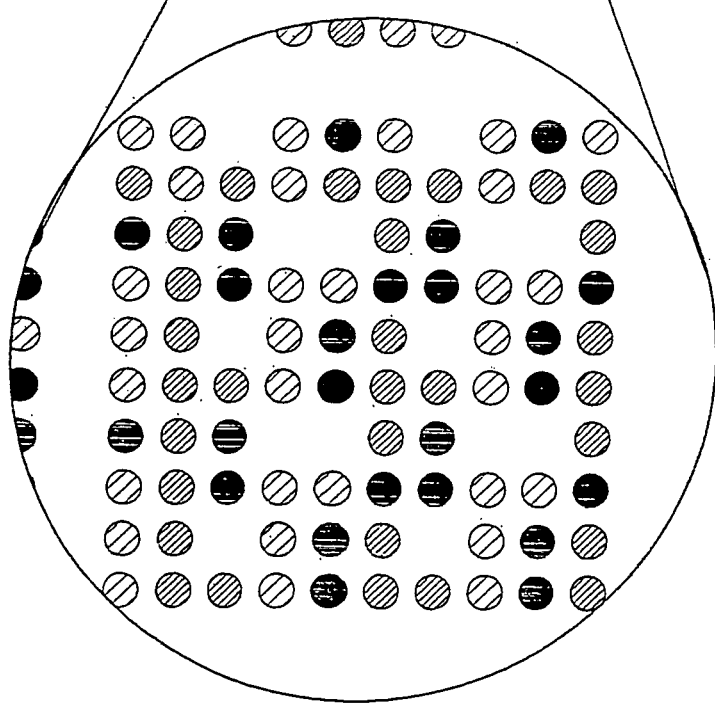

US 7,200,254 B2

PROBE REACTIVE CHIP, SAMPLE ANALYSIS APPARATUS, AND METHOD THEREOF

CROSS REFERENCE TO RELATED APPLICATION

This application is a continuation-in-part application of U.S. application Ser. No. 10/115,864 filed on Apr. 4, 2002, now abandoned and claims the benefit of Japanese Application P2002-037418, filed Feb. 14, 2002, the entireties of which are incorporated herein by reference.

BACKGROUND OF THE INVENTION

1. Field of the Invention

The present invention relates to a method for analyzing a DNA microarray and a sample using the DNA microarray. More specifically, it relates to technology for improving accuracy and automating image analysis of the DNA microarrays by performing the alignment of a detection area defined by an analyzing tool and image correction relative to images of the DNA microarrays read via a scanner, in the image analysis of the DNA microarrays after hybridization.

2. Description of the Related Art

In recent years, genetic analysis has been implemented using DNA microarrays.

In this specification, DNA microarrays or DNA chips refer to the spotting of DNA in a grid-like pattern upon an array substrate comprising glass or the like.

Upon the DNA microarrays, DNA is spotted as probes capable of specifically reacting to marked DNA samples.

After an unknown DNA sample to be analyzed is run in onto the DNA microarrays and the sample has been given an optically detectable light-emitting or fluorescent mark, if there are parts of the DNA sample that have a complimentary relationship with the DNA upon the grid then those parts of the DNA sample are linked to the DNA on the grid and become double stranded. Those DNA to which the portions of the sample do not link are rinsed away, and the condition of the double-stranded DNA may be observed as images by illuminating the DNA samples to be determined, and reading them with a scanner. In other words, it is possible to analyze the existence of the required genes, whether or not genes appear, or the degree to which the genes appear by analyzing the distribution of marks which emit light on the DNA microarrays. In this manner, a set of DNA is constructed upon the DNA microarray, and then through replacement with the relevant set of DNA, gene mutations and expression levels of genes, etc., may be detected.

FIG. 1 illustrates a sequence of processing in such DNA microarray analysis.

As shown in FIG. 1, in the hybridization step 3, unknown DNA samples that are to be analyzed are given luminescent marks and dropped onto a DNA microarray 1, which includes a spot region 1a upon which the DNA have been mounted. Here, if it is found that the DNA samples have a complementary relationship with the DNA on the grid, they are linked and become double stranded. Next, in the wash step 5, when the hybridized DNA microarrays 1 are washed away with a prescribed cleaning liquid, all DNA which are not linked are washed away. In the scanning step 7, the amount of light emission of each spotted DNA (gene) is measured by directing a laser beam with a prescribed wavelength suitable for exciting the luminescent marks (for example, Cy3, or Cy5) and by scanning the rinsed DNA microarrays within a scanner unit. Images of the scanned DNA microarrays 1 are stored in the DNA microarray image file 11. In the analysis step 9, the DNA microarray image file 11 is read in, and analysis processing of the DNA microarrays is implemented. More specifically, in the analysis step 9, based on the image data that has been read in, the fluorescent intensity of each spot is calculated and various analyses are implemented.

It should be noted that the DNA microarray images, which are read in through the scanner not from the DNA microarray image file 11, may be entered sequentially in the analysis step 9.

The analysis results are recorded as digital data files 13, and may be output in a displayed format through a display unit 15 or output in a printed format through a printing unit 17 as necessary.

FIG. 2 illustrates an example of the DNA microarrays 1 used in DNA microarray analysis. As shown in FIG. 2, the DNA microarray 1 comprises blocks in which individual genes (hereafter, referred to as "spots") of complementary DNA (cDNA) are respectively arranged upon the grids of the substrate 2 in a matrix with a predetermined number thereof in each row and each column. It should be noted that spots arranged in a spot region 1a on the substrate 2 respectively correspond to each probe, each differing from each other, and having the base sequence thereof already decoded, wherein the arrangement positioning upon the substrate 2 is predetermined.

FIG. 3 illustrates an example of a template, which is applied to the DNA microarray image file 11 during analysis processing. As shown in FIG. 3, the template is divided into a plurality of fields, such as A through F, and there are a plurality of blocks (p×24 in FIG. 3), which are formed by detection areas (corresponding to each spot of the DNA microarray) arranged in a matrix of m-row by n-column (4×4 in FIG. 3), within each field. Address numbers, such as a through p and 1 through 24, are attached to the blocks in both the X and Y directions, and the position of each block can be represented, for example, as "a, 1" in each field.

In the above mentioned analysis step 9, the individual spots in the read DNA microarray scanned image are applied to the detection area of the template provided by the analysis tool. The positioning operation by applying the detection area to the image is referred to as the alignment. In the analysis step 9, the alignment (positioning) process must be performed correctly in order to correctly set the individual detection areas arranged upon the substrate 2 of the DNA microarrays, which is pre-defined for individual spots on the image, so that the analysis tool may calculate the fluorescent intensity of each spot on the DNA microarrays and perform the correct analysis. (In order to analyze the read image correctly, individual detection areas must be applied to the corresponding individual spots during this alignment.) During this alignment (positioning) processing, in the case where a misalignment is detected, the position of an imaging or detection spot must be compensated so as to be set correctly in the detection area of the corresponding template.

However, the conventional method for analyzing the DNA microarrays through the hybridization step 3 has the following problems that need to be solved.

Namely, these problems include the low machined precision of the substrate 2, which is formed from glass and which configures the DNA microarray, and development of chips/cracks and breakage therein; the misalignment that developments when putting the DNA microarrays on the scanner autoloader or when loading them into the scanner; the accidental error built into the mechanical precision of the autoloader, the scanner, and the like; and further, the microdust that attaches to the substrate 2 and inevitably leads to misalignment occurring in the image file of the DNA microarrays to be analyzed.

However, external dimensions of this substrate 2 used to configure the DNA microarrays have low accuracy because of the machined precision, chips/cracks, and breakage of the glass. Therefore, in practical use, the outside dimension itself of the substrate 2 cannot be used for aligning the DNA microarrays and template provided by the analysis tool.

Accordingly, multiple DNA microarrays are set onto the autoloader, and the DNA microarrays are continuously scanned by the scanner to automate the accumulation of image data 11. In the following analysis step 9, it is then necessary to manually detect the misalignment caused by misalignment in θ direction (rotational misalignment), misalignment in x direction, and misalignment in y direction, and manually align the detection area for the DNA microarray image file 11, or else determine whether or not the alignment of the detection area performed by the existing analysis apparatus makes an error.

In particular, in cases where misalignment of the image is extreme, the alignment processing cannot be performed in the correct manner using automation.

Accordingly, DNA microarray image file detection area alignment processing and detection area alignment success/ failure determination is dependent on human observation and judgment, and the inability to automate this has created a bottleneck in the processing.

In particular, in the case where there is a large number of pages of the images to be analyzed, the alignment processing of these detection areas and determination of whether the alignment has been successful or unsuccessful for the detection area requires a large amount of time and labor. Moreover, as inkjet techniques have been adapted to technology for spot formation upon the DNA microarrays, due to the increased miniaturization of spot diameters as well as increasingly high-pitched intervals between spots, performing proper alignment processing manually or through visual observation has become especially difficult.

SUMMARY OF THE INVENTION

The present invention was conceived in order to solve the foregoing technical problems, one of its objects being to provide a DNA microarray, sample analysis apparatus and sample analysis method to carry out the alignment of a detection area with a DNA microarray image file quantitatively and automatically with high accuracy in the DNA microarray analysis.

Moreover, another object of the present invention is to provide a DNA microarray, sample analysis apparatus and sample analysis method to carry out the success/failure alignment determination processing quantitatively and automatically with high accuracy.

Moreover, another object of the present invention is to enable parallel analysis processing and labor savings and expedited analysis processing by enabling unattended consecutive execution of steps until the desired analysis data is obtained via the scanning step through analysis step.

In the embodiments of the present invention described below, a reference pattern, which is utilized for the alignment of a detection area with a DNA microarray image file, is provided on the surface of a substrate of a DNA micro array to be analyzed, and the alignment processing and alignment correction processing in high accuracy are carried out by utilizing the reference pattern of the DNA microarray.

This reference pattern may comprise a combination of spots that always emit light and spots that never emit light.

Moreover, in the embodiments of the present invention described below, the alignment processing is performed in a plurality of phases: by DNA microarray, by spot, and by block.

One aspect of the present invention is A probe reactive chip, comprising: a substrate; a spot region in which spots for fixing a probe capable of specifically reacting to a sample, which is marked so as to be optically detectable, are formed in a matrix on a surface of the substrate; and a reference pattern area, which is arranged within the spot region or approximate to the spot region, comprising a plurality of different alignment marks in order to correct a misalignment of the spots during analysis of the sample on the surface of the substrate.

The reference pattern area may comprise a combination of spots that always emit light and spots that never emit light.

The spot region may comprise a plurality of blocked spot sub-regions on the surface of the substrate; and the reference pattern areas are arranged within the spot sub-regions, respectively.

The spot region may comprise a plurality of blocked spot sub-regions on the surface of the substrate; and the reference pattern areas are arranged within the spot sub-regions, respectively.

The spot that always emits light within the reference pattern area may be a fluorescent material emitting light at a predetermined fluorescent intensity or greater.

The spot that always emits light within the reference pattern area may be a nucleic-acid binding material.

The spot that always emits light within said reference pattern area may be one or more of a housekeeping gene, fragments of the housekeeping gene, or a nucleic acid including the housekeeping gene or the fragment in a base sequence thereof.

The reference pattern area may comprise a plurality of spots that never emit light being arranged surrounding a spot that always emits light.

The probe reactive chip may further comprise a reference mark, which is for correcting misalignment of the spot region and which is arranged outside of the spot region on a surface of the substrate.

The reference mark may be a fluorescent material emitting light at a predetermined fluorescent intensity or greater.

The reference mark may be a nucleic-acid binding material.

The reference mark may be one or more of a housekeeping gene, fragments of the housekeeping gene, or a nucleic acid including the housekeeping gene or the fragment in a base sequence thereof.

The reference mark may comprise a plurality of spots that always emit light, or a combined array of spots that always emits light and spots that never emit light.

The reference mark may indicate chip inherent information including chip type and a manufactured lot identifier.

The spot sub-regions may be arranged having the interval with another adjacent spot sub-region be at least double the length of each spot interval within a spot region arranged within said spot sub-regions.

Another aspect of the present invention is a sample analysis apparatus comprising: a reference pattern information memory unit, which defines information for a reference pattern that is formed on a probe reactive chip and that comprises a plurality of different position marks for correcting a spot misalignment; an image data read in unit, which reads in image data acquired by scanning a spot for fixing a probe capable of specifically reacting to a sample upon the probe reactive chip that is marked so as to be optically detectable; an image data alignment unit, which aligns the image data with a predefined detection target area based on reference pattern area information read from the reference pattern area information memory unit, and generates correction data for correcting misalignment of the image data and the detection target area; a determination unit, which determines success/failure of said alignment by analyzing image data aligned with the image data alignment unit; a correction unit, which correct misalignment of the image data and the detection target area based on the correction data; and an analysis unit, which analyzes the corrected image data, and outputs digitalized data relating to the sample.

The reference pattern area information stored in the reference pattern information memory unit may be a pattern comprising a combination spots that always emit light and spots that never emit light.

The reference pattern area information stored in the reference pattern information memory unit may be a relative coordinate from a reference mark.

The reference pattern area information stored in the reference pattern information memory unit may be a relative coordinate between the reference patterns.

The reference pattern area information may be defined for each of a plurality of blocked spot sub-regions on the probe reactive chip in the reference pattern memory unit; and the image data alignment unit aligns the image data by the spot sub region.

The analysis unit selectively operates in either automatic mode or manual mode; and the determination unit repeatedly performs analysis of the aligned image data a predetermined number of times, and adds information indicating that alignment processing for the chip has failed to output data in the case where a desired analysis result cannot be obtained.

The sample analysis apparatus may further comprise a scanning unit, which acquires said image data by scanning a spot for fixing a probe capable of specifically reacting to a sample upon the probe reactive chip that is marked so as to be optically detectable; wherein the scanning unit and the analysis unit execute processes in parallel.

The image data alignment section comprises: a first alignment unit, which aligns a spot of the image data with a detection area by each spot in the image data; and a second alignment unit, which aligns the image data by a plurality of blocked spot sub-regions on the probe reactive chip.

The sample analysis apparatus may further comprise a third alignment unit, which aligns the image data by the entire spot region using a reference mark.

Another aspect of the present invention is a sample analysis method comprising: defining reference pattern area information comprising a plurality of different position marks formed on a probe reactive chip for correcting misalignment of a spot in a reference pattern information memory unit; reading in image data acquired by scanning a spot for fixing a probe capable of specifically reacting to a sample upon the probe reactive chip and marked so as to be optically detectable; aligning the image data to a predefined detection target area based on reference pattern area information read from the reference pattern area information memory unit and generating correction data for correcting misalignment of the image data and the detection target area; determining whether success/failure of the alignment by analyzing the aligned image data; correcting a misalignment of the image data and the detection target area based on the correction data; and analyzing the corrected image data and outputting digitalized data relating to the sample.

The reference pattern area information stored in the reference pattern information memory unit may be a pattern comprising a combination of spots that always emit light and spot that never emit light.

The reference pattern area information stored in the reference pattern information memory unit may be a relative coordinate from a reference mark.

The reference pattern area information stored in the reference pattern information memory unit may be a relative coordinate between said reference patterns.

The reference pattern area information may be defined for each of a plurality of blocked spot sub-regions on the probe reactive chip in the reference pattern information memory unit; and the aligning of image data aligns the image data by the spot sub-regions.

The analyzing may function in either automatic mode or manual mode, selectively; and the determining may repeatedly perform analysis of the aligned image data a predetermined number of times, and may add to output data information indicating that alignment processing for the chip has failed in the case where the desired analysis result cannot be obtained.

The sample analysis method may further comprise a scanning step for acquiring the image data by scanning a spot for fixing a probe capable of specifically reacting to a sample upon the probe reactive chip and marked so as to be optically detected; wherein the scanning and the analyzing are performed in parallel.

The image data aligning may comprise: a first alignment step for aligning a spot of the image data to a detection area by each spot in image data; and a second alignment step for aligning the image data by a plurality of blocked spot sub-regions on the probe reactive chip.

The sample analysis method may further comprise: a third alignment step for aligning the image data by the entire spot region using a reference mark.

Another aspect of the present invention is a program for causing a computer execute a sample analysis process, comprising: processing for defining in a reference pattern information memory unit information for a reference pattern area that is formed on a probe reactive chip and comprises a plurality of different position marks for correcting a spot misalignment; processing for reading in image data acquired by scanning a spot for fixing a probe upon the probe reactive chip and capable of specifically reacting to a sample marked so as to be optically detectable; processing for aligning the image data to a predefined detection target area based on reference pattern area information read from the reference pattern information memory unit and generating correction data for correcting misalignment of the image data and the detection target area; processing for determining success/failure of the alignment by analyzing the aligned image data; processing for correcting misalignment of the image data and the detection target area based on the correction data; and processing for analyzing the corrected image data and outputting digitalized data relating to the sample.

The reference pattern area information stored in the reference pattern information memory unit may be a pattern comprising a combination of spots that always emit light and spots that never emit light.

The reference pattern area information stored in the reference pattern information memory unit may be a relative coordinate from a reference mark.

The reference pattern area information stored in the reference pattern information memory unit may be a relative coordinate between the predefined reference patterns.

The reference pattern area information is defined for each of a plurality of blocked spot sub-regions on the probe reactive chip in the reference pattern information memory unit; and the processing for aligning image data aligns said image data by the spot sub-regions.

The analysis processing may function in either automatic mode or manual mode, selectively; and the determination processing may repeatedly execute an analysis for the aligned image data for the predetermined number of times, and may add information indicating that alignment processing for the chip is failed in the case where the desired analysis result cannot be obtained to output data.

The program may further include: scanning processing for acquiring the image data by scanning a spot for fixing a probe upon the probe reactive chip and capable of specifically reacting to a sample marked so as to be optically detectable; wherein the scanning processing and the analysis processing are executed in parallel.

The image data alignment processing may comprise: a first alignment processing for aligning a spot of the image data to a detection area in units of each spot in image data; and a second alignment processing for aligning the image data in units of a plurality of blocked spot sub-regions on the probe reactive chip.

The program may further comprise: a third alignment processing for aligning the image data in units of the entire spot region using a reference mark.

Another aspect of the present invention is a program for causing a computer to execute a sample analysis process, comprising: processing for defining in a reference pattern information memory unit information for a reference pattern area that is formed on a probe reactive chip and comprises a plurality of different position marks for correcting a spot misalignment; processing for reading in image data acquired by scanning a spot for fixing a probe upon the probe reactive chip and capable of specifically reacting to a sample, which is marked so as to be optically detectable; processing for aligning the image data to a predefined detection target area based on reference pattern area information read from the reference pattern area information memory unit and generating correction data for correcting misalignment of said image data and the detection target area; processing for determining success/failure of the alignment by analyzing the aligned image data; and processing for correcting misalignment of the image data and the detection target area based on the correction data.

BRIEF DESCRIPTION OF THE DRAWINGS

FIG. 27 is a diagram illustrating an example of the display screen image of a scanned image of the DNA microarrays provided by the analysis control unit 363 according to an embodiment of the present invention;

DETAILED DESCRIPTION OF THE EMBODIMENT

Hereafter, a DNA microarray (DNA chip), a sample analysis apparatus, and a method thereof are described in detail, while referencing FIGS. 4 through 33.

In this embodiment, detection area alignment processing and misalignment correction processing are implemented on a DNA microarray image file, providing a reference mark, which is used for detection area alignment of a DNA microarray image file, is provided upon the DNA microarray substrate to be analyzed, and in addition, a reference pattern, which is utilized for the alignment processing mentioned above as well as misalignment correction processing, is deployed within a block comprising the spot region of the DNA microarrays. In addition, in this embodiment, the alignment processing is performed in a plurality of phases: by DNA microarray, by spot, and by block.

Figure 1:
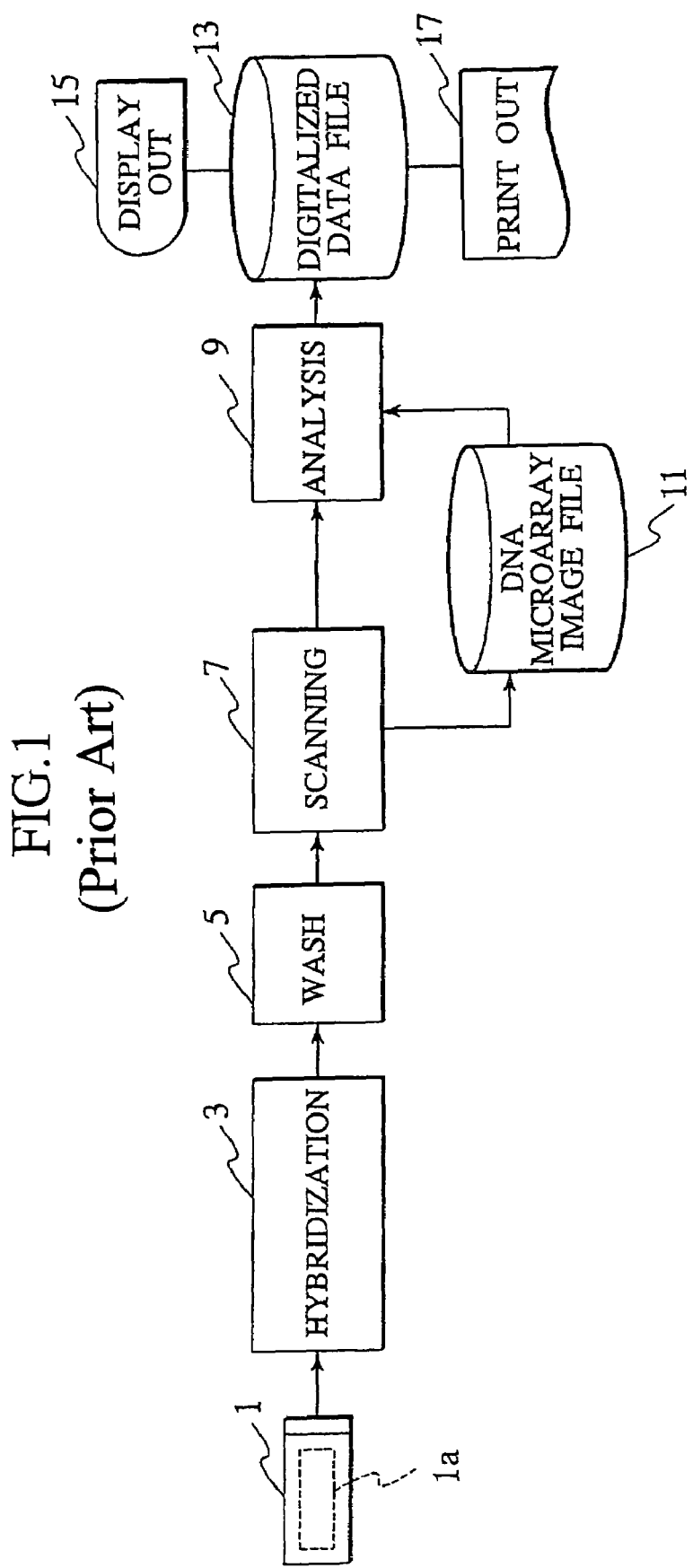
FIG. 1 is a schematic diagram illustrating a series of steps of sample analysis using DNA microarrays.
Figure 2:
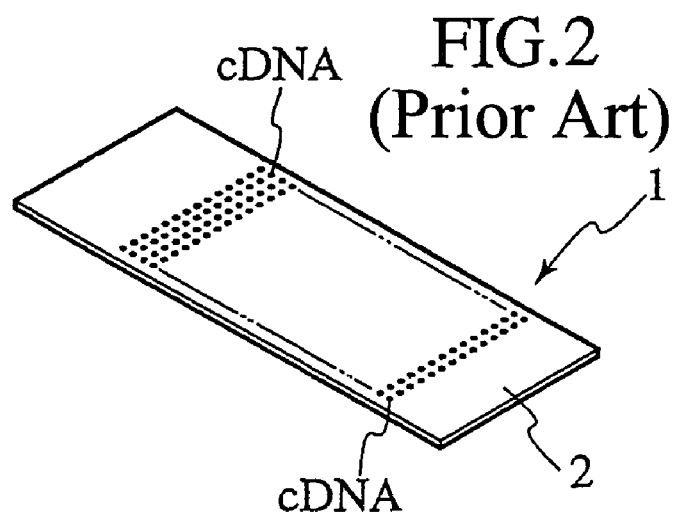
FIG. 2 is an oblique perspective view illustrating an example of the DNA microarrays.
Figure 3:
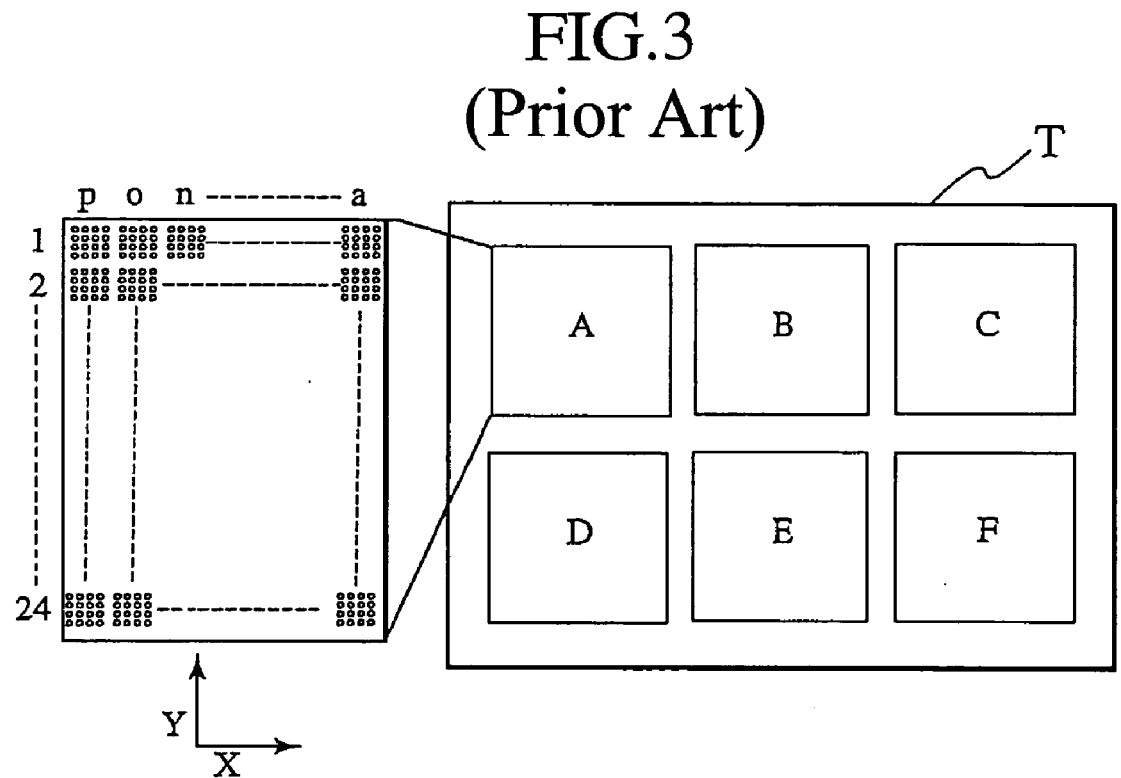
FIG. 3 is a diagram illustrating an example of the arrangement of the detection area of the template used in the sample analysis step.
Figures 4, 5:
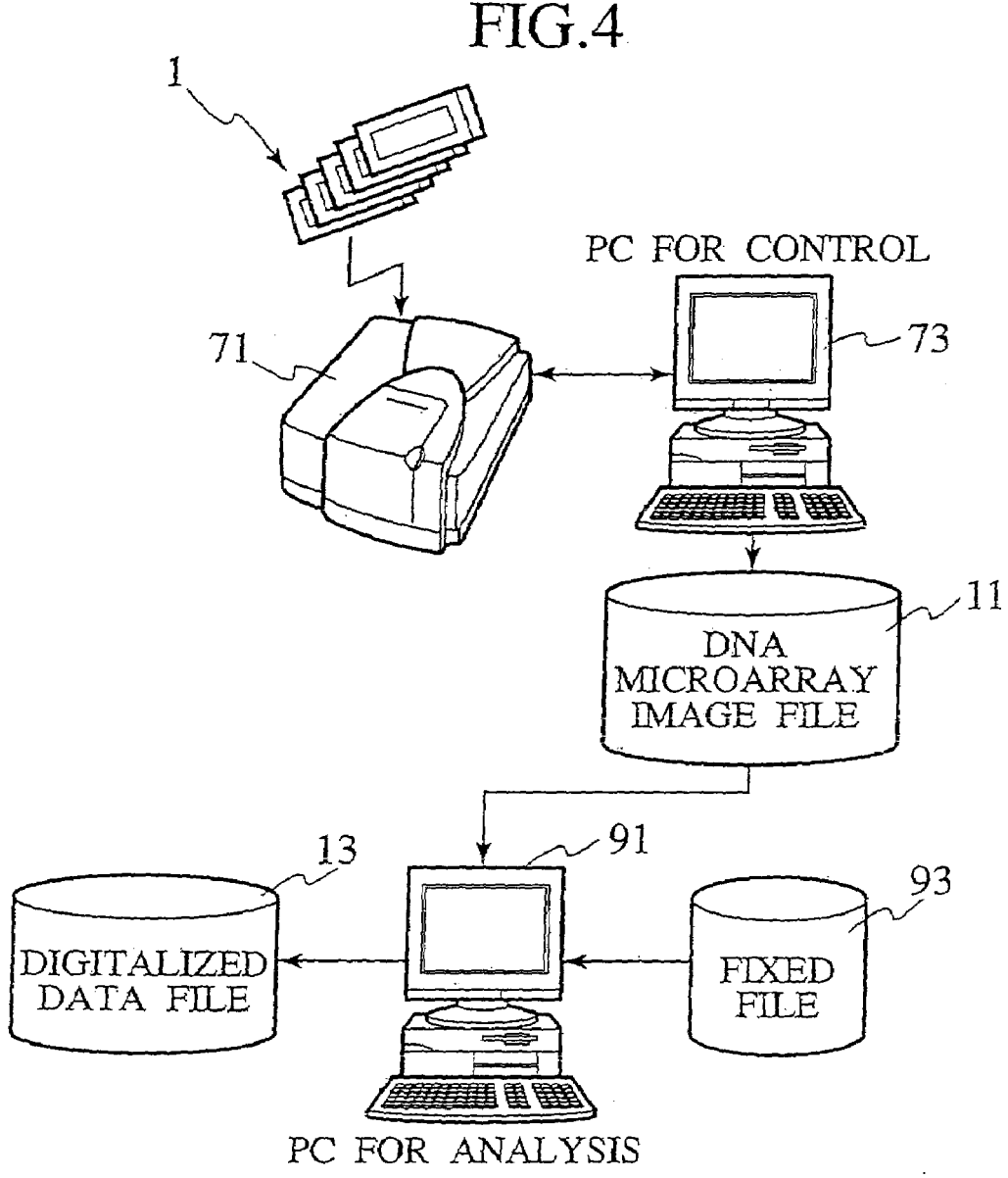
FIG. 4 is a block diagram illustrating an example of the hardware structure of the sample analysis apparatus according to an embodiment of the present invention.
FIG. 5 is a diagram illustrating an example of image data digitalized by the sample analysis apparatus according to an embodiment of the present invention.

FIG. 4 is a block diagram illustrating the overall configuration of a sample analysis system according to an embodiment of the present invention.

As shown in FIG. 4, the sample analysis system according to this embodiment comprises a scanner unit 71, a control computer 73, and an analysis computer 91.

The scanner unit 71, which comprises an autoloader mechanism for loading a plurality of DNA microarrays 1, uses a laser to excite the DNA microarrays on which the DNA samples marked with a fluorescent marker are dropped and stores the obtained image in a DNA microarray image file 11. The DNA microarrays 1 are scanned at excitation wavelengths corresponding to, for example, fluorescent dyes Cy3 and Cy5, respectively, obtaining for each one of the DNA microarrays 1 an image file corresponding to each respective excitation wavelength. The image file may be, for example, a 16-bit grey-scale Tiff format image; however, it is also allowable for it to be another Multi-Image Tiff format image or a JPEG format image.

The control computer 73 may be, for example, a personal computer capable of connecting to the scanner unit 71 via a LAN cable, such as a general-purpose personal computer, and controls scanning as well as image acquisition of the DNA microarrays 1 by the scanner unit 71.

The analysis computer 91 reads in the DNA microarray image file 11. Alternatively, the DNA microarray image that is read in directly from the scanner unit 71 or the control computer 73 may be entered. A group of analysis definition files 93, which define the parameters for implementing analysis, is then additionally read in, analysis of the DNA microarray image is performed, and digitalized analysis result data is output to a digitalized data file 13. A program, which acts as an analysis tool for performing analysis processing according to this embodiment, is installed into the analysis computer 91. This analysis program should act as a program for executing the analysis processing according to this embodiment and may utilize or be based in part on "GenePix Pro"™, for example, which was developed by InterMedical Co., Ltd. and runs under Microsoft Windows.

An analysis program running on the analysis computer 91 performs automated control of the analysis of the DNA microarray image file 11, and while the details of the processing contents will be described later, in short, it reads in the DNA microarray image file 11, reads in a group of analysis definition files 93, and performs the alignment processing (alignment processing using a reference mark) so as to match a reference mark on the read DNA microarray image to a reference position on the template to be stored in the group of analysis definition files 93. Moreover, the analysis program implements alignment processing by spot (spot-by-spot alignment processing) on the DNA microarrays based on the image data and the detection area, as well as alignment processing for image data by block (block-by-block alignment processing), each comprising a plurality of spot regions on the DNA microarray, using the reference pattern. When there is an alignment error, the analysis program automatically corrects the misalignment of the image file by matching with the detection area.

In the case where the image files to be processed cannot be digitalized within a predetermined time period, the analysis program reattempts analysis processing a predetermined number of times, then if the number of reattempts exceeds the predetermined number of times, outputs information indicating the digitalization error for that image to a log file in order to give notice that manual digitalization should be performed. The analysis program ends with outputting the digitalized image data information to a digitalized data file 13.

It should be noted that this analysis computer 91 may be provided in plural for a scanner unit 71/control computer 73 pair, and this plurality of units perform analysis processing for a large amount of image files in parallel. In addition, even if this scanner unit 71/control computer 73 pair is not provided, the DNA microarray image file 11 may be read in through other means.

The group of analysis definition files 93 comprises, more specifically, an analysis parameter file 931 and an analysis automation information definition file 933.

The analysis parameter file 931 includes the following information:

Array definitions of the blocks and spots upon the DNA microarrays (such as the number of blocks in each row and column, the number of spots in each row and column, and the diameter of a spot)

Definitions of information for block/spot position upon the DNA microarrays

Definitions of gene identification information, such as the gene name corresponding to each spot Definitions of the attributes for each spot (for example, whether it is a "non-existent spot", "good spot", or "bad spot"). (It should be noted that there are attributes that vary in the alignment process, such as a "not found spot".)

The analysis automation information definition file 933 includes the following information:

Specification of the image file generation method (in conjunction with/independent of scanning by the scanner unit)

Definitions of the analysis target image file name and specification of the digitalized data storage destination Definitions of the reference marks used for the above-mentioned alignment that uses reference marks (such as the number of reference marks, minimum fluorescent intensity, coordinates, recognition area, and the amount of allowable misalignment)

Definitions of the reference patterns for alignment determination (such as the number of reference patterns, minimum fluorescent intensity, coordinates, and the amount of allowable misalignment)

Definition of the number of reattempts (or maximum wait time) in the case where no image file exists Definition of the retry method for incorrect alignment (such as the number of reattempts or maximum wait time, detection area shift order and shift amount)

Figure 35:
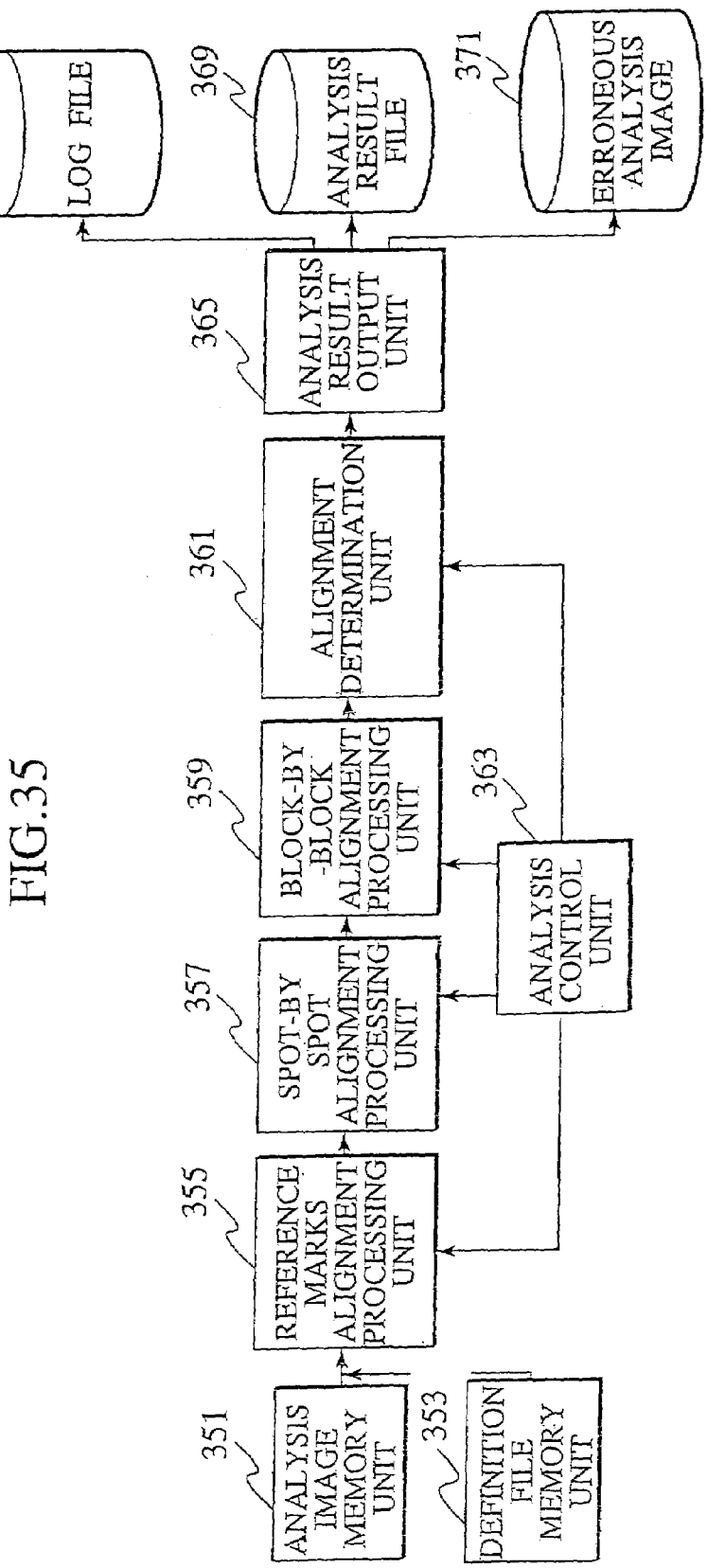
FIG. 35 is a diagram illustrating an example of the hardware structure of the sample analysis apparatus according to an embodiment of the present invention.

FIG. 35 is a block diagram illustrating the functional configuration of a sample analysis apparatus according to this embodiment. As shown in FIG. 35, the sample analysis apparatus according to this embodiment is an analysis computer 91 into which the above mentioned analysis program is installed and which comprises: an analysis image memory unit 351; a definition file memory unit 353; a reference mark alignment processing unit 355; a spot-by-spot alignment processing unit 357; a block-by-block alignment processing unit 359; an alignment determination unit 361; an analysis control unit 363; an analysis result output unit 365; a log file 367; an analysis result file 369; and an erroneous analysis image file 371. The analysis image memory unit 351 stores the DNA microarray image file 11 shown in FIG. 4.

Figure 6:
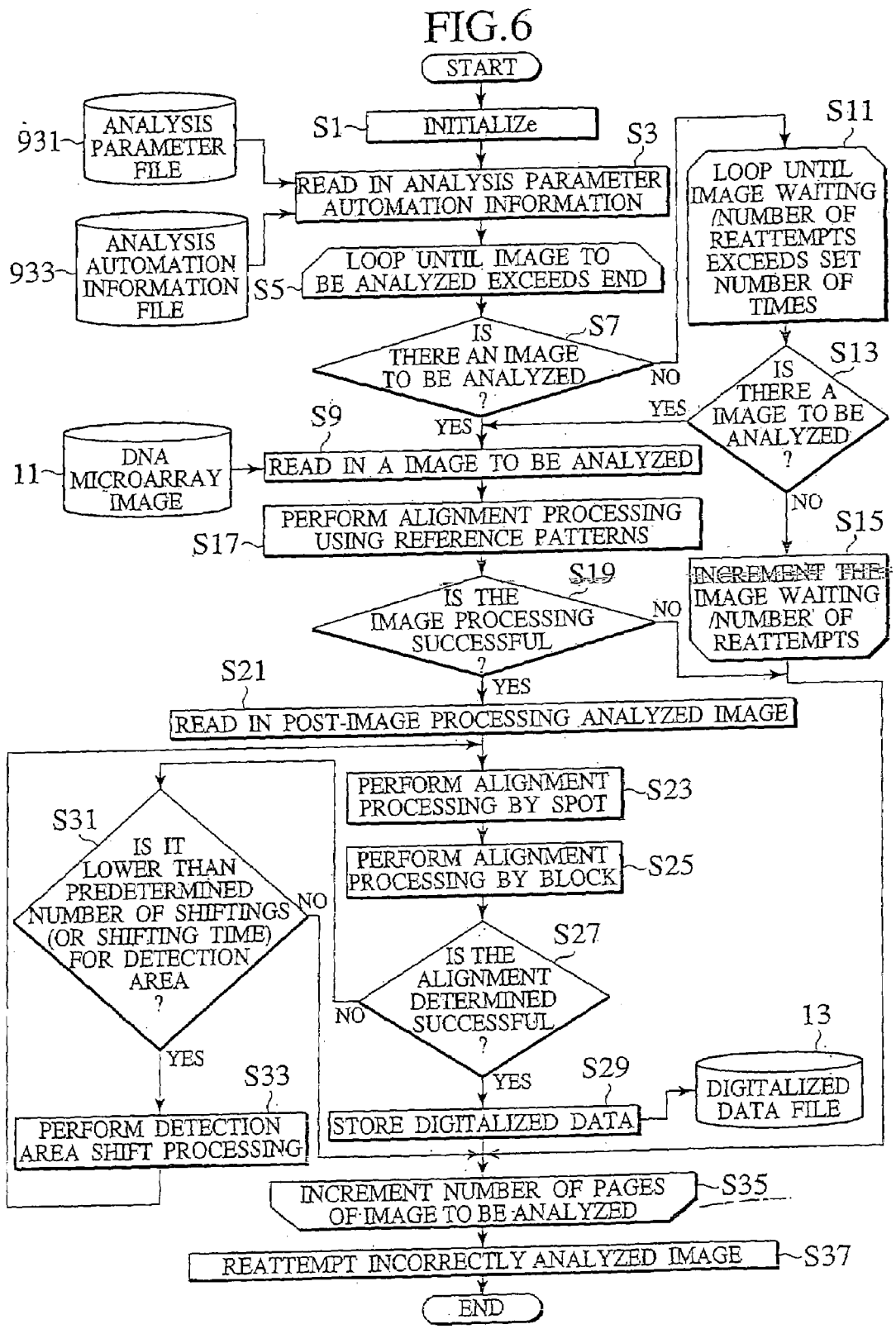
FIG. 6 is a flowchart illustrating an outline of processing procedures in the sample analysis method according to an embodiment of the present invention.

The definition file memory unit 353 stores the group of definition files shown in FIG. 4 (the analysis parameter file 931 and analysis automation information file 933 shown in FIG. 6). This definition file memory unit 353 corresponds to the reference pattern information memory unit in the claims. The reference mark alignment processing unit 355 includes the image data read in unit mentioned in the claims. The reference mark alignment processing unit 355, the spot-by-spot alignment processing unit 357, and the block-by-block alignment processing unit 359 correspond to the image data alignment unit and correction unit mentioned in the claims. The alignment determination unit 361 corresponds to the determination unit mentioned in the claims. The analysis control unit 363 and the analysis result output unit 365 correspond to the analysis unit mentioned in the claims.

It should be noted that the analysis image memory unit 351, the definition file memory unit 353, the reference mark alignment processing unit 355, the spot-by-spot alignment processing unit 357, the block-by-block alignment processing unit 359, the analysis control unit 363, the alignment determination unit 361, and the analysis result processing unit 365 are all mounted on the analysis computer 91 shown in FIG. 4. The analysis computer 91 may be a single unit, or alternatively, a plurality thereof may be connected over a network and configured as an analysis computer system.

FIG. 5 illustrates an example of a portion of the digitalized data output from the analysis computer 91. As shown in FIG. 5, digitalized data is collected as fluorescent intensity data regarding the respective spots detected in, for example, the Cy3 excitation wavelength and Cy5 excitation wavelength. More specifically, digitalized data 13 includes the following information relative to each spot:

Flag for a detection spot

Block number

Row and column numbers within a block

Gene identification information including the gene name

Center coordinate (x, y) of a detection spot

The median, mean, and standard deviation of the fluorescent intensity of the detection spot in the Cy3 excitation wavelength The median, mean, and standard deviation of the fluorescent intensity of the detection spot surroundings (background) in the Cy3 excitation wavelength The median, mean, and standard deviation of the fluorescent intensity of the detection spots in the Cy5 excitation wavelength The median, mean, and standard deviation of the fluorescent intensity of the detection spot surroundings (background) in the Cy5 excitation wavelength Various data relating to quality Next, procedures for sample analysis processing in the sample analysis method according to this embodiment are described.

FIG. 6 is a flowchart illustrating procedures for sample analysis processing in the sample analysis method according to an embodiment of the present invention.

To begin with, analysis program initializes and the processing is begun (step S1). Next, the analysis parameter file 931 and analysis automation information file 933 are read in (step S3). The reading in of the analysis automation information file 933, allows, for example, the name of the analysis image definition file, the name of the analysis parameter file, the number of image waiting reattempts, and the image waiting time to be read. The name of the analysis image definition file specifies the image and the number of pages to be analyzed to the analysis program.

Processing from step S5 through step S35 is repeatedly executed until the number of pages of the image to be analyzed reaches the total number of pages of the image that has been read in (i.e., end conditions End are met) (step S5).

Next, whether or not there is an image to be analyzed is determined (step S7), and if there is no image to be analyzed (step S7N), the number of times to reattempt image waiting is read in step S3, and processing from step S11 through step S15 is repeatedly performed until the number of times set in the analysis program is exceeded. Moreover, whether or not there is an image to be analyzed is determined (step S13), and if there is an image to be analyzed (step S13Y), processing proceeds to step S9, meanwhile if there is no image to be analyzed obtained (step S13N), the counter of the number of times to reattempt image waiting is incremented (step S15), and if the set number of times is exceeded, processing proceeds to step S35.

Returning to step S7, if there is an image to be analyzed (step S7Y), the corresponding image file is read in from the DNA microarray image file 11 as the DNA microarray to be analyzed (step S9). Otherwise, the image file to be analyzed may be entered directly from the scanner unit 71 and control computer 73 bypassing the DNA microarray image file 11. Continuing, alignment processing using the reference marks (above mentioned reference mark alignment processing) is performed (step S17). After executing alignment processing using the reference marks in step S17, image processing is performed on the image data (step S19), and if the image processing is determined to have failed (step S19N), the processing proceeds to step S35. Meanwhile, if the image processing is determined to have been a success, the post-image processing image file is read in (step S21).

Next, alignment processing is performed by spot on the DNA microarrays (the above-mentioned spot-by-spot alignment processing) (step S23), and in addition alignment processing by block is performed on the DNA microarrays (the above-mentioned block-by-block alignment processing) (step S25). It should be noted that it does not matter whether step S23 or step S25 is performed first, as long as they are performed after the analysis image read processing in step S21 and before the alignment determination in step S27.

Whether alignment is successful or not sucessful is determined based on the image data digitalized after the reference mark alignment processing and the spot-by-spot alignment processing (step S27). If alignment is determined to be successful (step S27Y), the digitalized image data is output to the digitalized data file 13, and the counter of the number of pages of the image to be analyzed is incremented (step S35). Meanwhile, if the alignment is determined to have been a failure (step S27N), then it is determined whether the predetermined number of times of detection area shifting (or shift times) has been exceeded (step S31), and if the predetermined number of detection area shift times has been reached (step S31N), then processing proceeds to step S35. Meanwhile, if the predetermined number of detection area shift times has not yet been exceeded (step S31Y), then detection area shift processing (correction processing) by block of the DNA microarrays is performed (step S33), and the processing returns to the spot-by-spot alignment processing in step S23.

More specifically, during the detection area shift (correction) processing in step S33, under the assumption that alignment using reference marks is for the most part correct, alignment of a spot/detection area pair is attempted starting with small shifts and gradually becoming larger shifts as clockwise rotation progresses.

Finally, after completion of the analysis of all images to be analyzed, processing from step S7 through step S35 may be repeatedly performed the predetermined number of times for the image in which the analysis error occurs (step S37).

Next, the detail of each alignment processing in this embodiment is described. In the alignment processing of this embodiment.

(1) to begin with, light-emitting reference marks are arranged on the DNA microarrays. In addition, reference patterns comprising positive controls and negative controls are arranged within a block on the surface of the DNA microarray substrate 2 (or in the vicinity of the block). At a minimum, information indicating the positional relationship between the reference marks and each block, and information indicating the positional relationship between the array pattern of the reference pattern and each block are registered in advance and known as analysis automation information of the DNA microarrays.

(2) After recognition/detection of a reference mark upon an image, it is applied to the detection area on which each of spots have been defined beforehand on the template (reference mark alignment processing) by correcting (rotating/shifting) the image to the normal position (designed position) of the reference mark using the coordinates of the position of the reference mark defined beforehand as template analysis automation information. Thereafter, application of each detection area on the template to each spot is performed (spot-by-spot alignment processing).

(3) On the scanned image, array patterns (reference patterns) comprising positive controls and negative controls are detected through pattern matching using the pattern information and position information of the reference pattern defined beforehand in the template, specification of the position is performed, and alignment is performed by block (block-by-block alignment processing).

Figure 7:
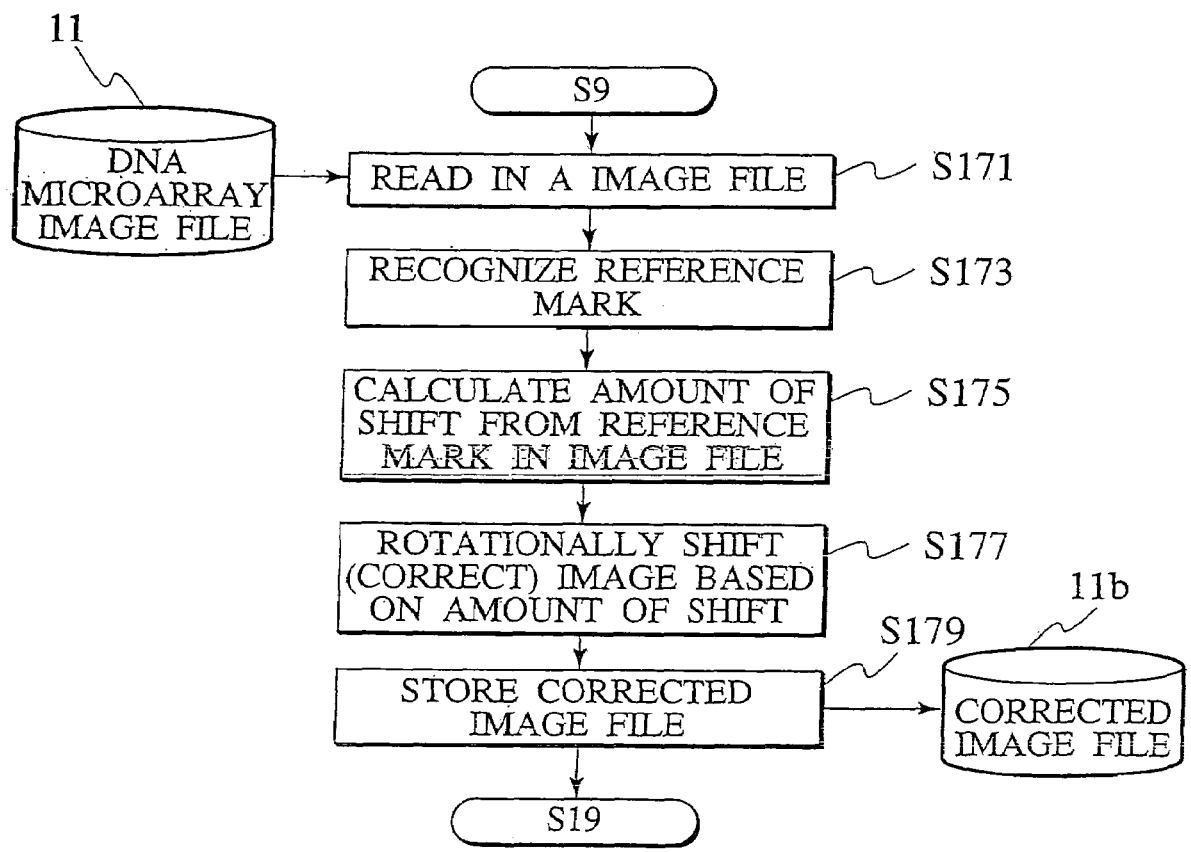
FIG. 7 is a flowchart illustrating detail of the processing procedures in alignment processing using a reference mark in step S17 shown in FIG. 6.

FIG. 7 is a flowchart describing in more detail the reference mark alignment processing in step S17 shown in FIG. 6 with the reference mark according to this embodiment.

As shown in FIG. 7, the reference mark analysis processing unit 355 according to this embodiment reads in the DNA microarray image file (step S171), and automatically recognizes the template including the reference pattern recognition area, which has been read in from the analysis automation information file 933 in advance, and in addition performs analysis (digital) processing of the image file and aligns the reference marks so as to match the reference pattern of the read image file to the reference pattern definition positioned within the reference pattern recognition area on the template.

Figure 8:
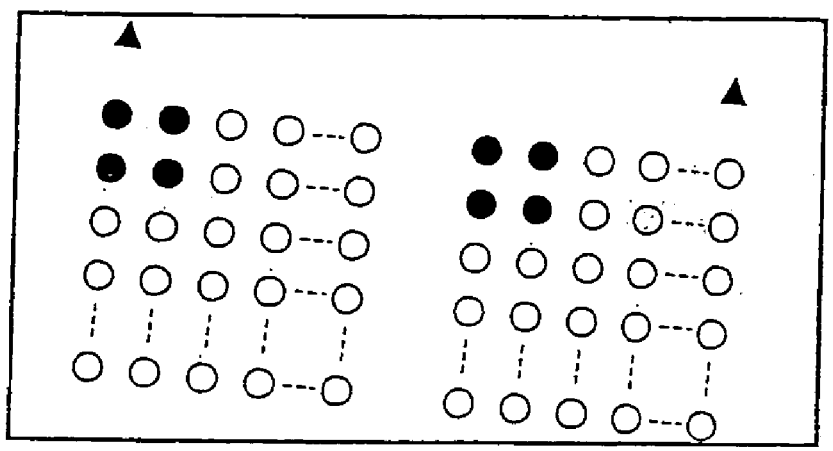
FIG. 8 is a diagram illustrating an example of a representation of an image of the DNA microarrays read in by the sample analysis apparatus according to an embodiment of the present invention.

FIG. 8 illustrates an example of the image file that is read in step S171.

As shown in FIG. 8, the reference marks used for the reference mark alignment processing according to this embodiment have been arranged in the periphery of the spot region where the spots have been pre-arranged on the substrate.

This reference mark may be a mark made by a material that gives off a luminescent signal when the DNA microarrays are scanned by the scanner unit 71, for example, fluorescent materials, such as autofluorescent materials, nucleic-acid binding materials, housekeeping genes, a fragment of the housekeeping genes, or nucleic acid including the housekeeping gene or the fragment in a base sequence thereof may be used.

It should be noted that in this specification the autofluorescent material is a material that naturally has fluorescence as one of its inherent physical properties. The autofluorescent material gives off a fluorescent signal when the DNA microarrays are scanned. The nucleic-acid binding material should be a material that absorbs fluorescent-marked nucleic acid within a sample to be dropped on the DNA microarrays although it may not have fluorescence as one of its inherent physical properties, for example, a polyallylamine may be used. Since the nucleic-acid binding material absorbs the fluorescent-marked nucleic acid, it gives off a fluorescent signal when the DNA microarrays are scanned. Housekeeping genes are genes naturally appearing within a living organism in amounts having a constant minimum, and do not have fluorescence as a physical property. Since the hybridization always occurs with the fluorescent marked nucleic acid within the sample fluid, if the housekeeping genes are spotted on the DNA microarrays, a fluorescent signal is also emitted when the DNA microarrays are scanned. When these autofluorescent materials, nucleic-acid binding materials, and housekeeping genes are all spotted on the DNA microarrays, they become spots having the characteristic of always emitting light when they are scanned, and these are referred to as positive controls in this specification. On the contrary, the spots having the characteristic of not always emitting light when they are scanned are referred to as negative controls in this specification.

Figure 9:
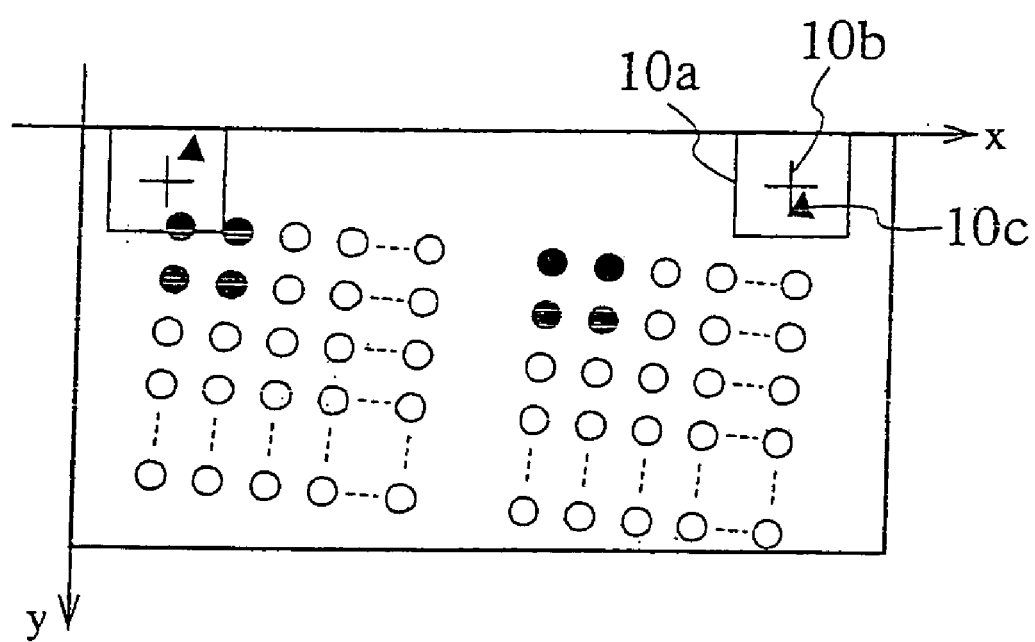
FIG. 9 is a diagram illustrating a condition where the template stored in a definition file memory unit 353 overlaps a representation of the image shown in FIG. 8.
Figure 10:
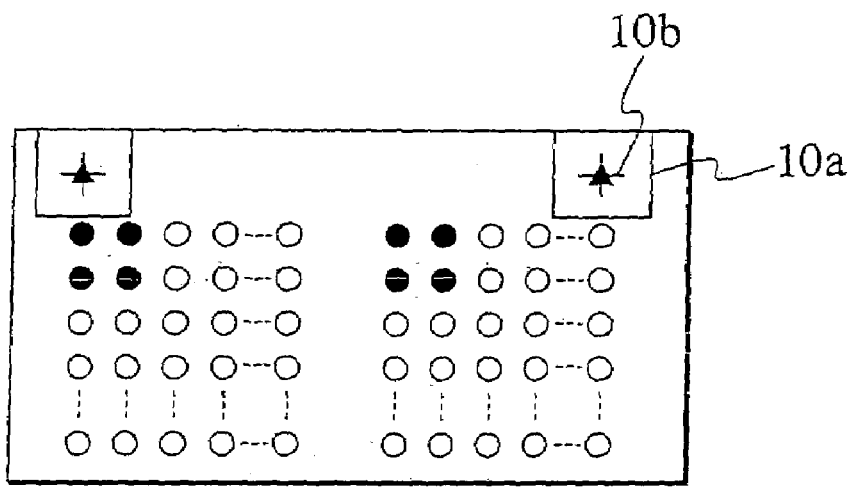
FIG. 10 is a diagram illustrating a condition after the image shown in FIG. 9 is aligned with an alignment processing unit 355 using a reference mark according to an embodiment of the present invention.

FIG. 9 illustrates a status that the template including the reference mark recognition area is automatically recognized relative to the image shown in FIG. 8, which has been read in through the scanner unit 71. In FIG. 9, a situation where a misalignment occurs between a reference mark definition position 10b within the reference mark recognition area 10a on the template and a reference mark 10c within the image file, which has been read in, is illustrated. The analysis program corrects the position from this misaligned state so as to fit the reference mark 10c within the image file to the reference mark definition position 10b on the template, as shown in FIG. 10. It should be noted that the reference mark recognition area 10a and the reference pattern definition position 10b on the template are illustrated for convenience, thus it is not necessary for it to be visibly represented as an actual image.

According to alignment processing using the reference marks, the entire DNA microarrays (i.e., the entire spot region on the array) is substantially aligned relative to the entire template.

Returning to FIG. 7, the amount of shift according to the misalignment of the definition position 10b of the reference mark in the reference mark recognition area 10a of the template and the reference mark 10c in the image file, which is read in, shown in FIG. 9 is calculated (step S175), and the image is rotated and shifted based on the calculated amount of shift as shown in FIG. 10 (step S177). In the end, the corrected image file is stored in an image file 11b in which the post-correction image files are stored. It should be noted that the storage location may be an image file 11, from which the image file is read in step 171.

Next, a detail of the spot-by-spot alignment processing (step S23 in FIG. 6) in this embodiment is described.

Figure 11:
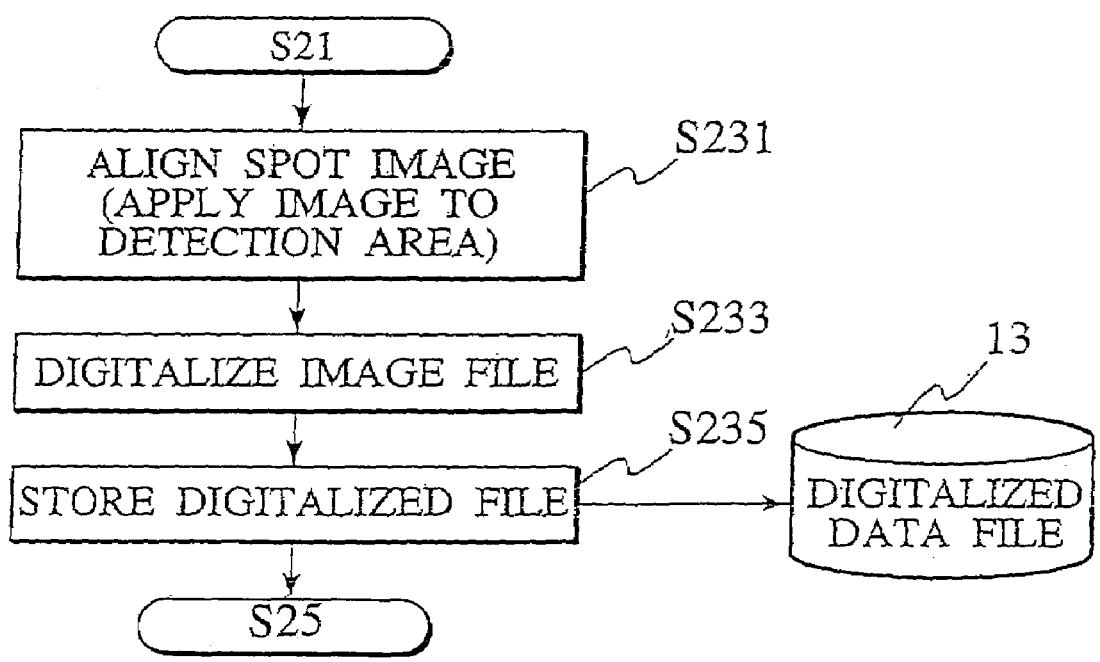
FIG. 11 is a flowchart illustrating detail of the processing procedures in the spot-by-spot alignment processing in step S23 shown in FIG. 6.

FIG. 11 is a flowchart describing the details of the spot-by-spot alignment processing in step S23 shown in FIG. 6, which is performed by spot on the DNA microarrays according to this embodiment.

As shown in FIG. 11, the spot-by-spot alignment processing unit 357 according to this embodiment performs alignment (step S231) for each spot image in each DNA microarray in the post-position correction processing image file 11b (image processing), which is read in step S21, to the detection area corresponding to each spot of the template, which has been read in beforehand from the analysis automation information file 933.

Figure 13:
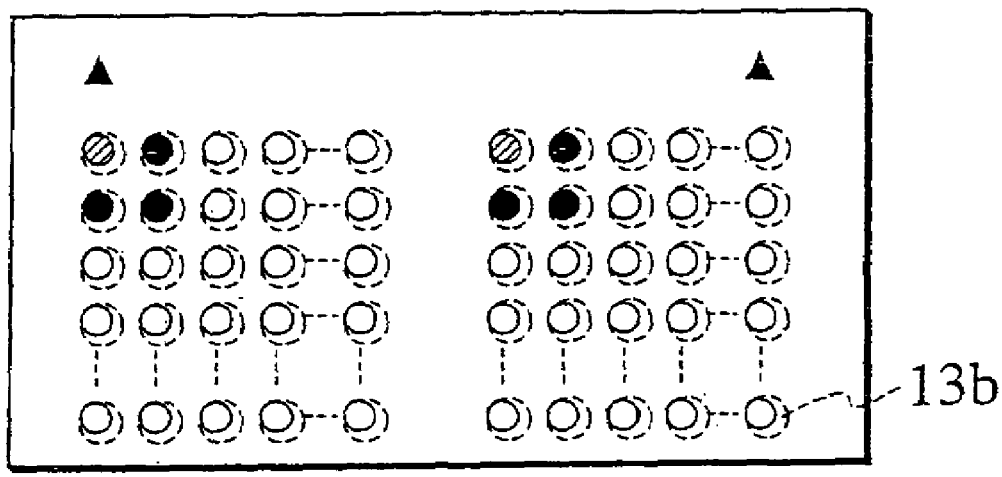
FIG. 13 is a diagram illustrating an example of the image read in by the spot-by-spot alignment processing unit 357 in step S21 shown in FIG. 6.

FIG. 13 illustrates a situation where each detection area of the template is applied to the DNA microarray image after position correction, which is read in step S21 shown in FIG. 6. In FIG. 13, the state where each detection area 13b of the template and each spot in the image file, which is read in, are misaligned is illustrated. The analysis program has the spot-by-spot alignment processing unit 357 perform positional correction so as to fit each spot image in the image file to each detection area on the template from this misaligned status as shown in FIG. 14.

Figure 14:
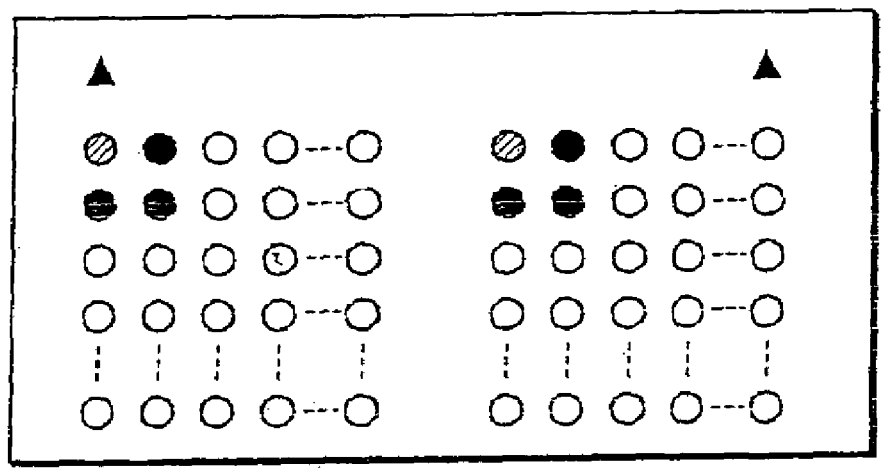
FIG. 14 is a diagram illustrating an example of the image shown in FIG. 13 after spot-by-spot alignment processing in step S23 shown in FIG. 6.

Returning to FIG. 11, the image file after position correction shown in FIG. 14 is digitalized based on the definition information of the template (step S233), and the digitalized file is stored in the digitalized data file 13 (step S235).

Next, the alignment processing by block (step S25 in FIG. 6) in this embodiment is described in further detail. In the alignment processing by block performed by the block-by-block alignment processing unit 359, both alignment processing by pattern matching using the pattern array of the reference pattern and alignment processing using reference pattern position coordinates are utilized. Alternatively, only one of the two may be performed.

Figure 15:
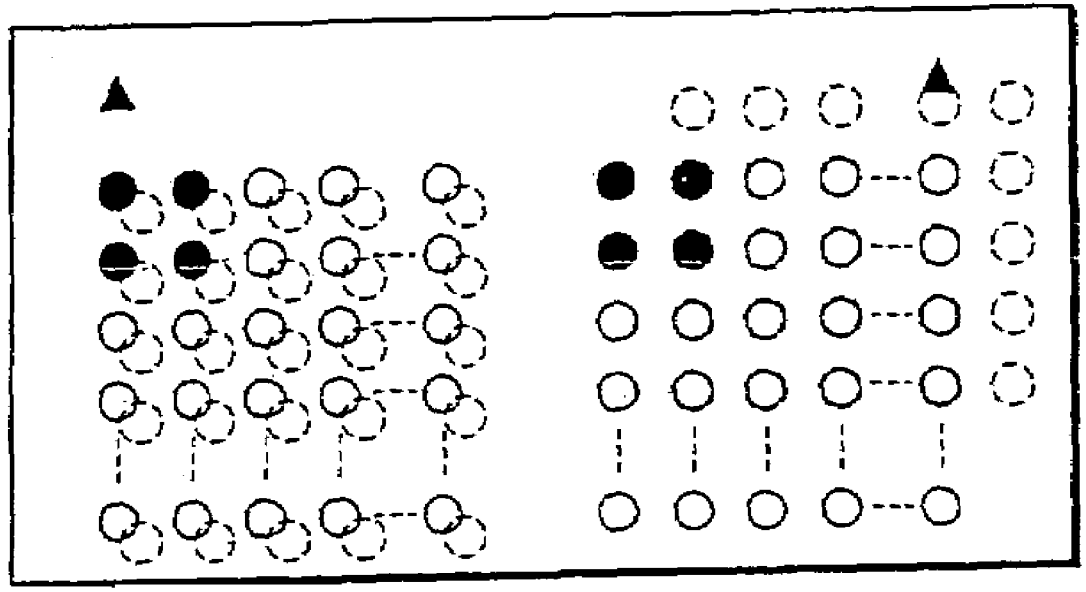
FIG. 15 is a diagram illustrating another example of the image shown in FIG. 13 after spot-by-spot alignment processing in step S23 shown in FIG. 6.

FIG. 15 illustrates an example of the DNA microarray image file, which is incorrectly aligned by the spot-by-spot alignment processing in step S23 of FIG. 6. As shown in FIG. 15, in the spot-by-spot alignment processing, the spot-by-spot alignment is executed by trying to match the detection area block on the template to a spot within a block for each block on the DNA microarrays. Accordingly, for example, if there should be a dust particle attached to the substrate of the DNA microarrays, the detection area to which each spot should be matched may be incorrectly determined, and an error in aligning the block may result. Accompanying miniaturization of the spot interval on the DNA microarrays, the above mentioned alignment error due to the occurrence of micro-dust is inevitable.

Accordingly, in this embodiment, reference patterns for adjusting block-by-block alignment are arranged beforehand within a block on the DNA microarrays, and the alignment error due to spot-by-spot alignment processing is adjusted.

Figure 12:
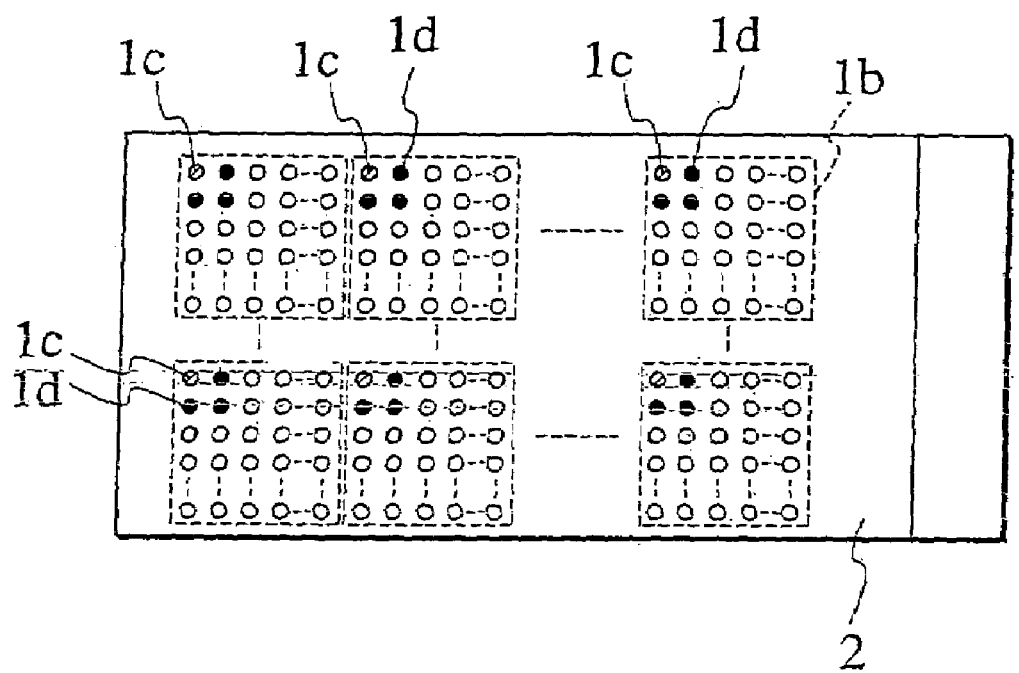
FIG. 12 is a diagram illustrating an example of the arrangement of the spots on the DNA microarrays according to an embodiment of the present invention.

FIG. 12 illustrates an example of the DNA microarrays used for this embodiment. As shown in FIG. 12, a plurality of groups of blocks 1b is arranged upon the DNA microarrays 1. Genes are spotted in each block, and in this embodiment, both positive controls, which are spots that always emit light, and negative controls, which are spots that never emit light (emission is rare), are arranged in each block. These positive controls and negative controls are normally used as markers in order to determine whether there are errors in the processing of the hybridization step. In this embodiment, reference patterns comprising combinations of these positive controls and negative controls are formed. This reference pattern is arranged within each block in which the spots for fixing genes, or probes, are formed in a matrix, thereby it may be regarded as the block-by-block alignment reference pattern for block-by-block alignment processing. This block corresponds to the spot sub-region mentioned in the claims.

It should be noted that positive control may be, similar to the above mentioned reference mark, a mark generated by a material, which emits a luminescent signal when the DNA microarrays are scanned by the scanner unit 71, for example, autofluorescent materials, nucleic-acid binding materials, housekeeping genes, fragments of the housekeeping genes, or nucleic acid including the housekeeping gene or the fragment in a base sequence thereof may be used.

More specifically, the positive controls are arranged within each block as shown by 1c in FIG. 12, while the negative controls are arranged surrounding them as shown by 1d. The reference patterns may be provided at a corner within a block or may be provided at the arbitrary position within the block. Or, it may be provided outside of, but approximately to, the blocks comprising the spot region, if necessary. Information regarding the pattern array and position coordinates of positive controls and negative controls arranged within the block is registered beforehand in the analysis automation information file 933 as one of the attribute information for the template. During the block-by-block alignment processing, spot positions within each block may be specified by executing the determination of the fluorescent intensity and position coordinates of these positive controls and negative controls.

Another pattern comprising positive controls surrounded by negative controls may be further deployed within the reference pattern in the block; alternatively, another pattern of positive controls surrounded by negative controls may be further deployed relative to a pattern within the block upon lines diagonal to the block. The erroneous determination due to the occurrence of dust in the DNA microarrays may be reduced by arranging other patterns to construct a plurality of reference patterns within one block.

Meanwhile, in the view of analyzing more genes using one DNA microarray, it is preferable that the area occupied with reference patterns comprising positive controls surrounded by negative controls be small.

FIGS. 18 through 23 illustrate examples of pattern arrangements of positive controls surrounded by negative controls according to this embodiment. It should be noted that in FIGS. 18 through 23, it is assumed that all genes other than the positive controls and negative controls within the block are spotted. In addition, the determination criteria for successful alignment in block-by-block alignment processing is that the fluorescent intensity of the positive control be a specified minimum fluorescent intensity or greater, but less than the threshold value, to which the positive control coordinates are pre-set as the attributes of the template.

Figure 18:
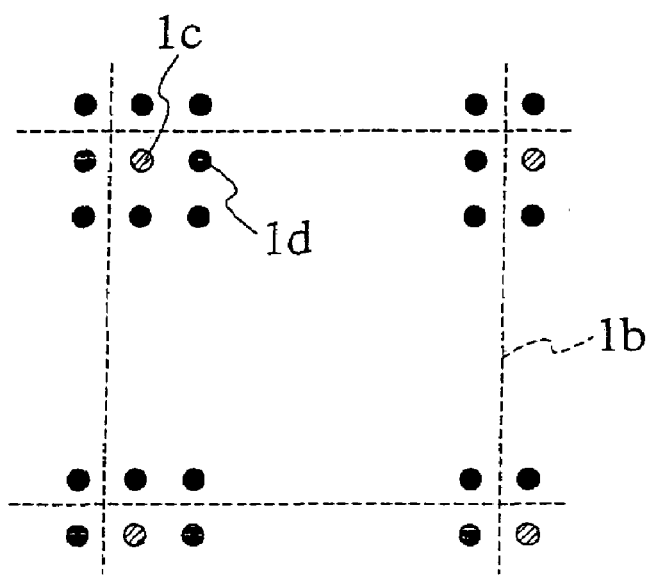
FIG. 18 is a diagram illustrating an example of a reference pattern arrangement comprising positive controls and negative controls within a block of the DNA microarrays according to an embodiment of the present invention.

In FIG. 18, the negative controls 1d are arranged astride a block 1b around one positive control 1c, thus the necessary number of positive and negative controls is nine per block. When this pattern is adopted, if one or more particles of dust having intensity stronger than the minimum fluorescent intensity exist on the periphery of the positive controls, they are incorrectly recognized as positive controls.

Figure 19:
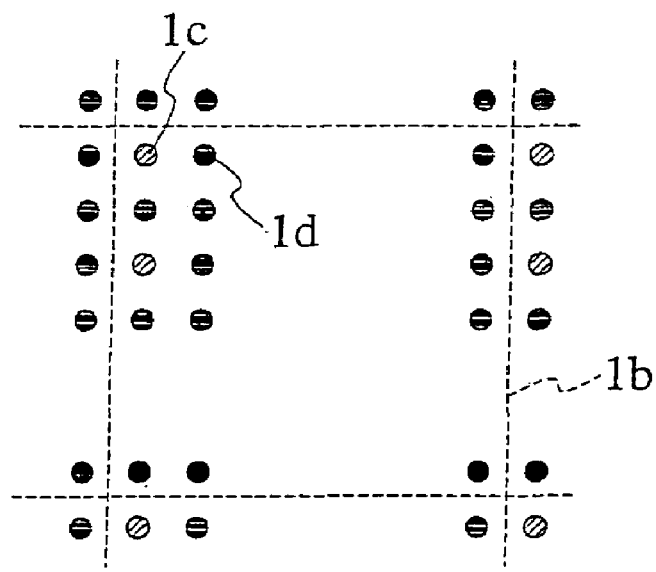
FIG. 19 is a diagram illustrating another example of the reference pattern arrangement comprising positive controls and negative controls within a block of the DNA microarrays according to an embodiment of the present invention.

In FIG. 19, the negative controls 1d are arranged astride the block 1b around two separated positive controls 1c, thus the necessary number of positive and negative controls is fifteen per block. When this pattern is adopted, if two or more particles of dust having intensity stronger than the minimum fluorescent intensity exist on the periphery of the positive controls, they are incorrectly recognized as positive controls.

Figure 20:
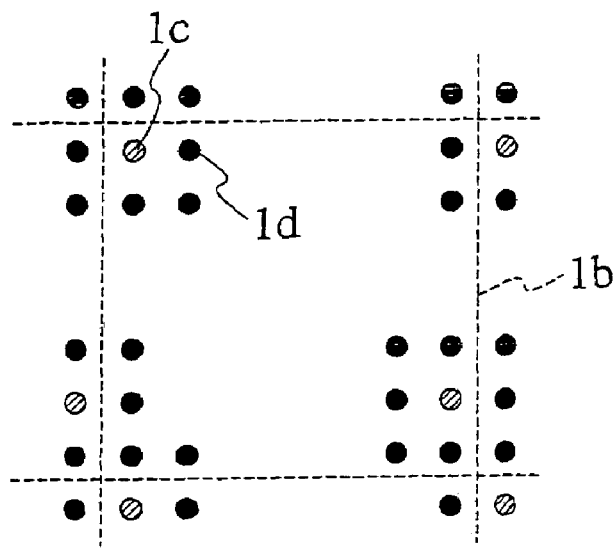
FIG. 20 is a diagram illustrating another example of the reference pattern arrangement comprising positive controls and negative controls within a block of the DNA microarrays according to an embodiment of the present invention.

In FIG. 20, the negative controls 1d are arranged astride the block 1b around one positive control 1c, and in addition, in the opposing corner of the block, the negative controls 1d are arranged surrounding one positive control 1c; thus, the necessary number of positive and negative controls is sixteen per block. When this pattern is adopted, if two or more particles of dust having intensity stronger than the minimum fluorescent intensity exist on the periphery of the positive controls, they are incorrectly recognized as positive controls. In the pattern shown in FIG. 20, the detection of rotational misalignment of the block is reinforced through comparison with the pattern of FIG. 18.

Figure 21:
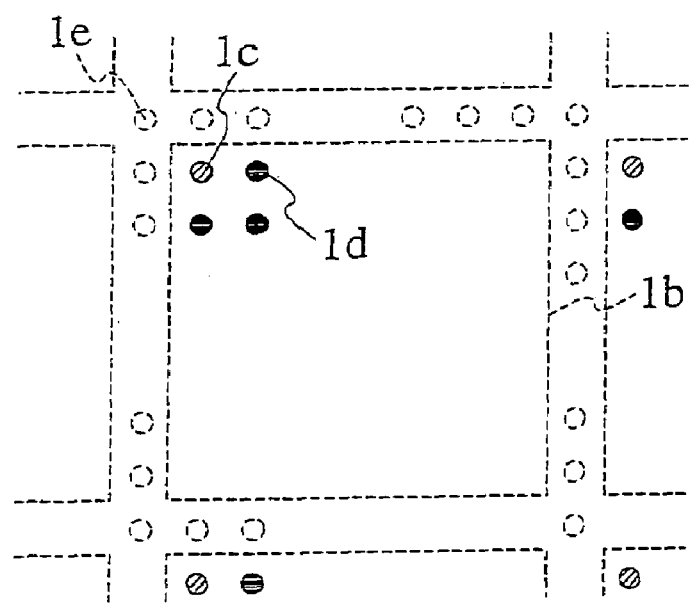
FIG. 21 is a diagram illustrating another example of the reference pattern arrangement comprising positive controls and negative controls within a block of the DNA microarrays according to an embodiment of the present invention.
Figure 22:
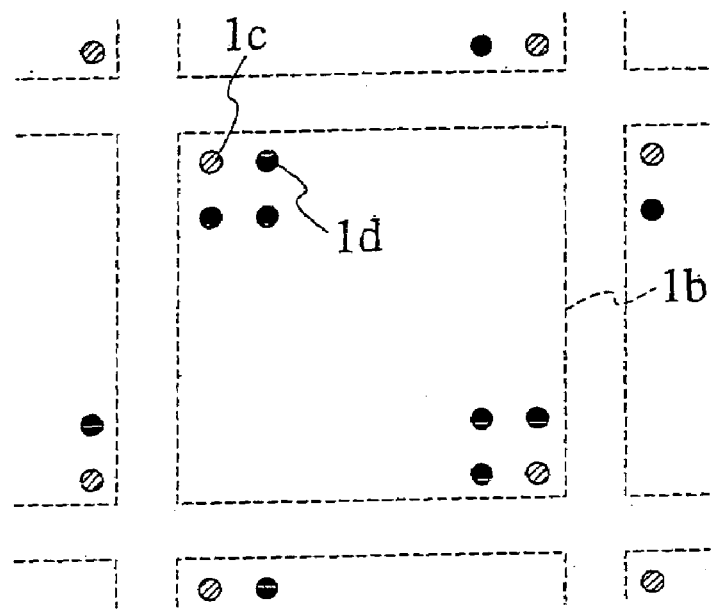
FIG. 22 is a diagram illustrating another example of the reference pattern arrangement comprising positive controls and negative controls within a block of the DNA microarrays according to an embodiment of the present invention.
Figure 23:
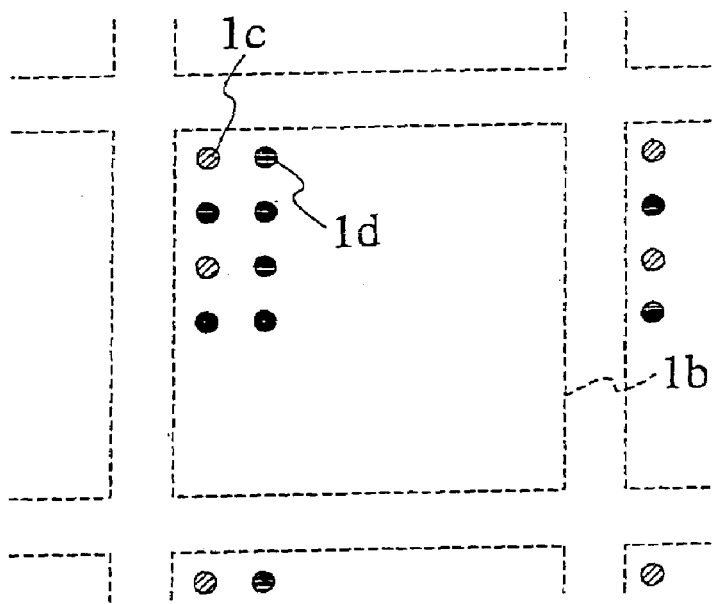
FIG. 23 is a diagram illustrating another example of the reference pattern arrangement comprising positive controls and negative controls within a block of the DNA microarrays according to an embodiment of the present invention.

In FIGS. 21 through 23, the block 1b pitch is at least twice the length of the spot pitch (i.e., there is an interval between the blocks 1b that correlates to one spot 1e).

With FIG. 21, the block 1b is arranged with an interval of at least one spot from the adjacent block 1b. The negative controls 1d are arranged around one positive control 1c, which is arranged in one of the four corners, thus the necessary number of positive and negative controls is four per block. When this pattern is adopted, if one or more particles of dust having intensity stronger than the minimum fluorescent intensity exist on the periphery of the positive controls, they are incorrectly recognized as positive controls.

With FIG. 22, the block 1b is arranged with an interval of at least one spot from the adjacent block 1b. Negative controls 1d are arranged around one positive control 1c, which is arranged in one of the four corners, and in addition, negative controls 1d are arranged in the opposing corner around one positive control 1c; thus, the necessary number of positive and negative controls is eight per block. When this pattern is adopted, if two or more particles of dust, which have intensity stronger than the minimum fluorescent intensity, exist with the same arrangement as the two positive controls on the periphery of the positive controls, they are incorrectly recognized as positive controls.

With FIG. 23, block 1b is arranged with an interval of at least one spot from the adjacent block 1b. The negative controls 1d are arranged around a positive control 1c, which is arranged at one of the four corners, and another positive control separated therefrom; thus the necessary number of positive and negative controls is eight per block. When this pattern is adopted, if two or more particles of dust having intensity stronger than the minimum fluorescent intensity exist with the same arrangement as the two positive controls on the periphery of the positive controls, they are incorrectly recognized as positive controls.

As can be understood from FIGS. 21 through 23, if the interval between blocks 1b is regarded as the pitch, and is at least twice the length of the spot pitch within the block, the necessity to enclose the positive controls with the negative controls astride the block is eliminated. Therefore, it may be possible to specify the position of the block with fewer numbers of positive and negative controls.

Figure 16:
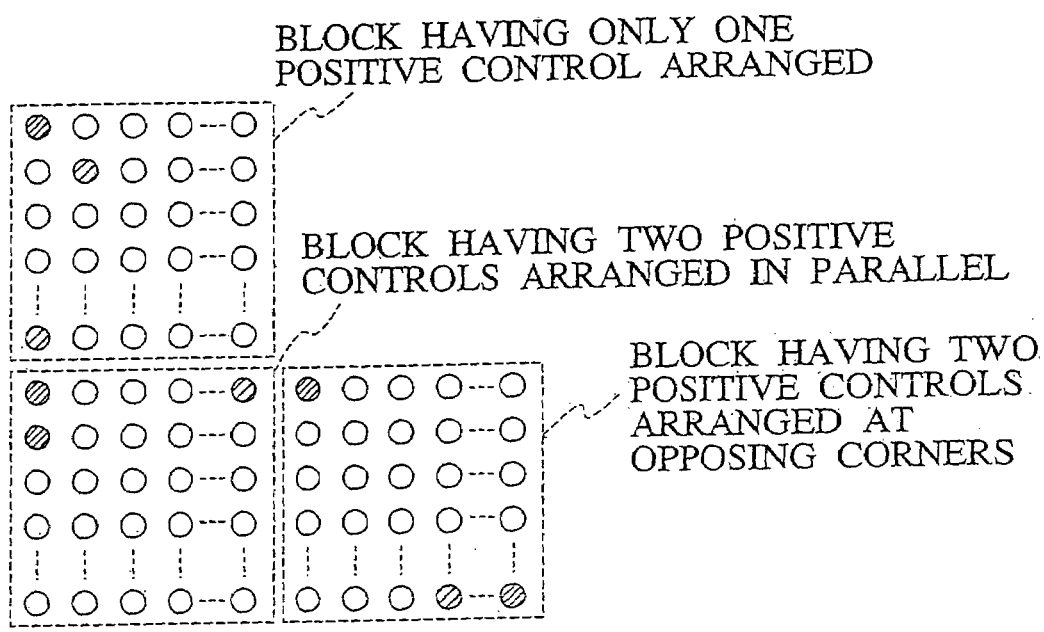
FIG. 16 is a diagram illustrating an example of a block of the DNA microarrays having a spot region in which positive controls are arranged according to an embodiment of the present invention.
Figure 17:
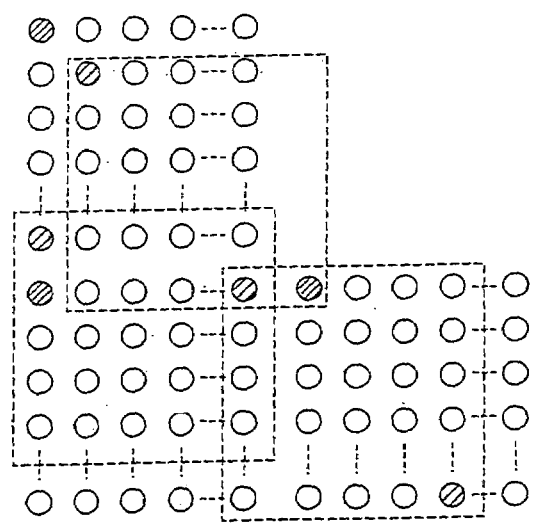
FIG. 17 is a diagram illustrating an example of a situation where the block shown in FIG. 16 is aligned incorrectly.

In the above mentioned FIGS. 18 through 23, the negative controls are arranged surrounding the positive controls; this arrangement is used in this embodiment for the following reasons. In other words, as shown in FIG. 16, for example, the arrangement of a block arranged with only one positive control, a block arranged with two positive controls side by side, and a block arranged with two positive controls in opposing corners, wherein negative controls are assigned, is assumed. FIG. 17 illustrates conditions after executing block-by-block alignment processing on a detection area upon a template by an analysis program in relation to the arrangement shown in FIG. 16. During determination of success/failure after block-by-block alignment processing, (1) to begin with, in the fluorescent intensity determination of the spot location, which is to be determined as the positive control, since DNA having a fluorescent intensity stronger than the threshold value exists, it is successful. (2) Next, since that in the position determination of the spot location, which is to be determined as the positive control, is greater than the allowable position coordinate misalignment, it is unsuccessful.

However, since miniaturization of spot intervals on the DNA microarrays is increasing, spot arrangement precision, reading precision of the scanner unit 71, the spot intervals from the post-hybridization spot shape, and the allowable amount of position coordinate misalignment become approximate. Therefore, in actuality, if the allowable amount of position coordinate misalignment is specified so that it is unsuccessful, although the alignment has been originally determined as being successful, it is unsuccessful and accurate success/failure determination is not achieved.

Meanwhile, by adopting the arrangement pattern according to this embodiment, which encloses the positive controls with the negative controls, the allowable amount of position coordinate misalignment may be specified as at least twice the length of the spot intervals. Therefore, significant and accurate success/failure determination for alignment may be implemented. It should be noted that without using determinations (1) and (2) even with determination using positive control and negative control pattern matching, as long as the post-alignment pattern and the pattern on the template do not have the same pattern array, it is valid since alignment is not determined as successful.

Figure 34:
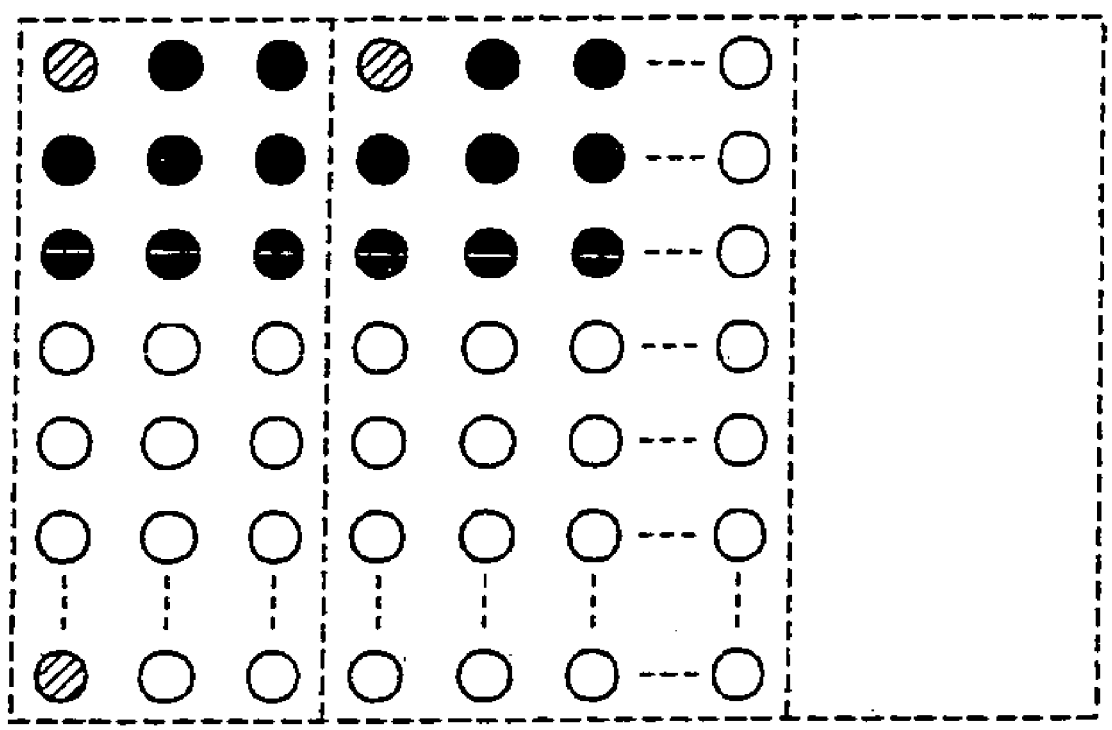
FIG. 34 is a diagram illustrating another example of the arrangement of the reference patterns on the DNA microarrays according to an embodiment of the present invention.

In addition, for example, if the allowable amount of misalignment can only be specified for triple the pitch due to spot position precision, machine precision and the like, the configuration in which the positive controls are doubly enclosed by the negative controls as shown in FIG. 34 is desirable. If there is by chance a DNA spot array having an array with the same fluorescent intensity, and it is incorrectly recognized when applying the detection area to the image, alignment may be accurately determined as unsuccessful through position coordination determination even though the positive controls and negative controls are determined as successful.

It should be noted that it is not necessary to use in combination the above-mentioned DNA microarrays and analysis processing in this embodiment, however, the above-mentioned DNA microarrays may be used for analysis programs other than the analysis program according to this embodiment.

Figure 24:
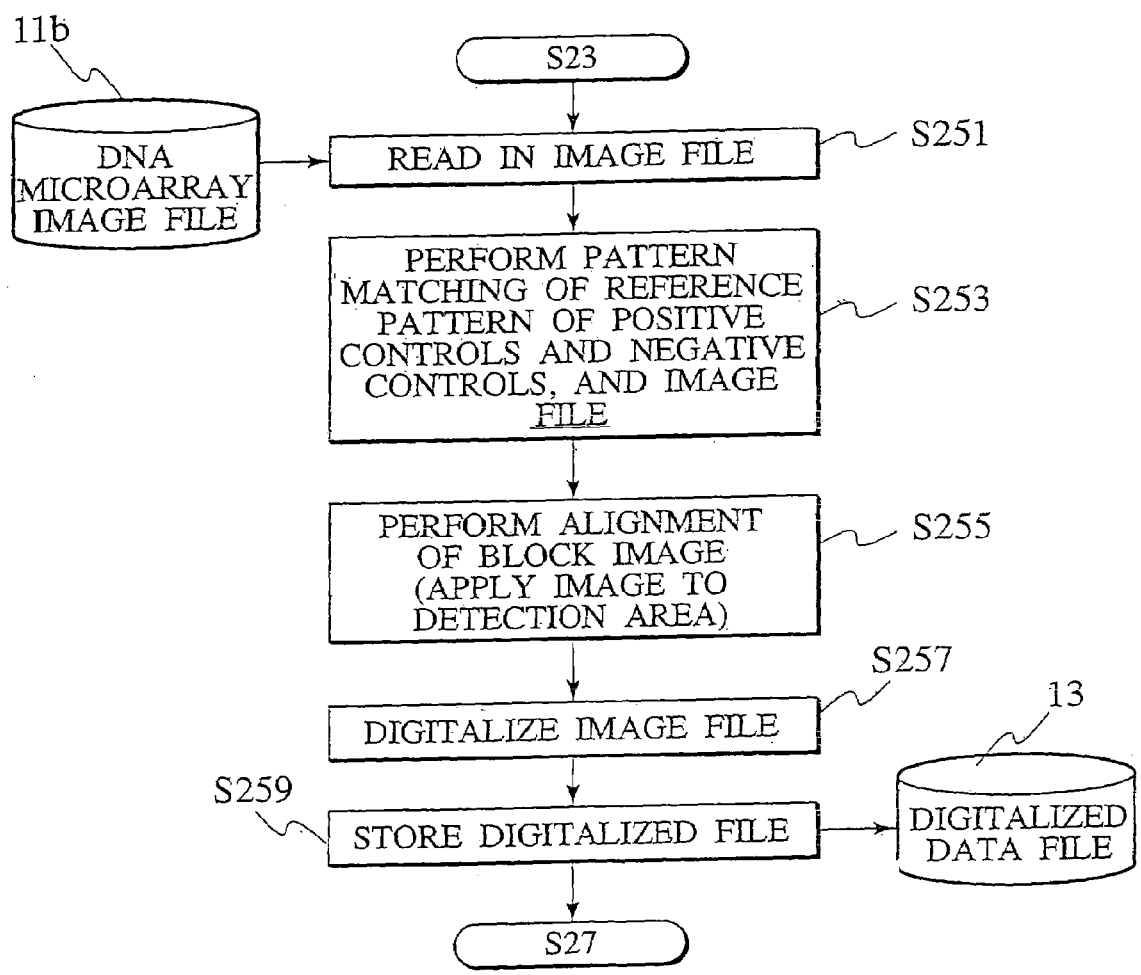
FIG. 24 is a flowchart illustrating detail of the processing procedures for block-by-block alignment processing in step S25 shown in FIG. 6.

FIG. 24 is a flowchart describing the detail of the block-by-block alignment processing in step S25 shown in FIG. 6, which is implemented block-by-block with the array pattern of the positive and negative controls on the DNA microarrays, according to this embodiment.

As shown in FIG. 24, the block-by-block alignment processing unit 359 according to this embodiment reads the image file 11b, which is read in step S21, after position correction processing (image processing) (step S251). Pattern matching between the reference patterns of the positive controls and negative controls pre-defined on the template and the image file is then performed (step S253). Otherwise, in this step S253, position coordinate determination may be used in conjunction with pattern matching or in exchange thereof.

As a result of this pattern matching, application of the block image to the detection area is reattempted, and the block image is aligned based on the calculated amount of shift (step S255). Based on the block-by-block alignment, the image file is digitalized (step S257), and the digitalized data is stored in the digital data file 13 (step S259).

Next, details of alignment success/failure determination processing conducted by an alignment determination unit 361 in this embodiment are described.

In other words, after completion of the above mentioned alignment processing using reference marks, spot-by-spot alignment processing, and block-by-block alignment processing, digitalization (analysis) of each spot is implemented, and determinations of number, fluorescent intensity, and position coordinates of the positive controls and negative controls are performed, and it is determined whether the alignment is properly executed.

Figure 25:
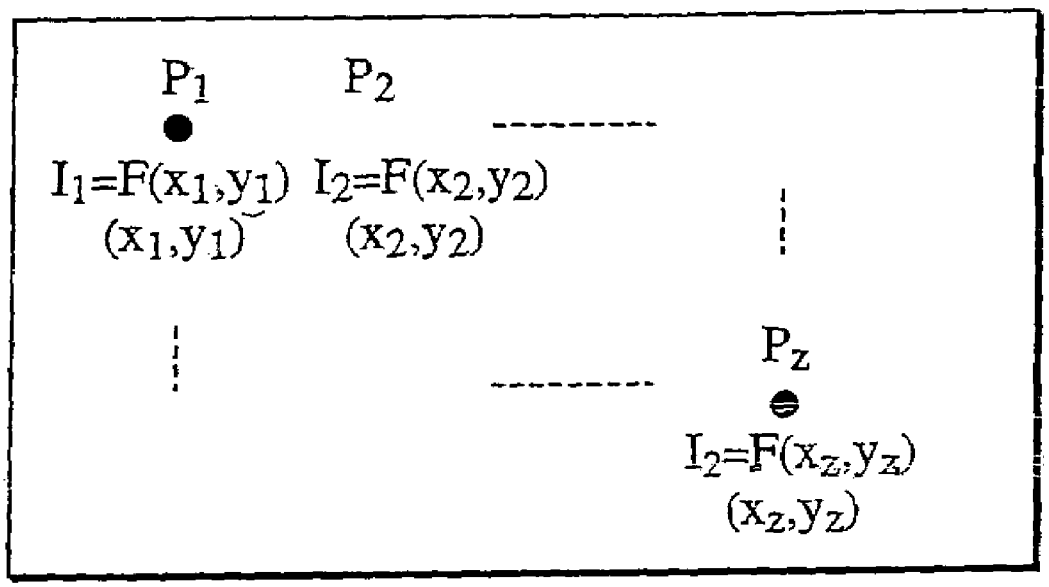
FIG. 25 is a diagram describing alignment determination processing in an embodiment of the present invention.

FIG. 25 illustrates an example of post-digitalized data of each spot.

In FIG. 25, Pn represents spots of interest (for example, positive controls). In represents the fluorescent intensity of Pn. (xn, yn) represents real coordinates of Pn upon an image. (Xn, Yn) represent coordinates of Pn in design. n is a natural number from 1 to Z.

(1) Determination Method Using the Fluorescent Intensity and Number of Positive and Negative Controls If the following conditions are all satisfied, the number and fluorescent intensity are determined as successful.

In the case where the positive controls of which the number is to be determined are denoted as Pn, that number is represented by Z.

In the case where the negative controls of which the number is to be determined are denoted as Pn, that number is represented by Z.

In the case where the to-be-determined positive controls are extracted from digitalized data as Pn, the minimum positive control fluorescent intensity $\leq$ In for n=1 to Z is satisfied.

In the case where the to-be-determined negative controls are extracted from digitalized data as Pn, In$\leq$the maximum negative control fluorescent intensity for n=1 to Z is satisfied.

(2) Determination Method Using Position Coordinates

Determination is executed using both or either one of the following determination methods.

Determination by absolute coordinates

If the following conditions are satisfied for n=1 to Z where the spots to be determined for position coordinates are denoted as Pn, position coordinate determination is successful.

$(|xn-xn| \leq$ amount of allowable misalignment in $x$ direction) and $(|Yn-yn| \leq$ amount of allowable misalignment in $y$ direction)

Determination by relative coordinates

P1 is regarded as the reference when the spot whereupon the position coordinate determination is to be implemented is denoted as Pn. In the case where the following conditions are satisfied for n=1 to Z, the position coordinate determination is successful.

$(|xn-x1| \leq |Xn-X1|+$amount of allowable misalignment in $x$ direction) and $(|yn-y1| \leq |Yn-Y1|+$amount of allowable misalignment in $y$ direction)

As a result of the above mentioned alignment determination processing (step S27 in FIG. 6), the analysis result output unit 365 stores digitalized data, of which alignment has been determined as successful, in the digital data file 13. Meanwhile, as for the image that does not obtain a successful alignment determination even with the predetermined number of re-alignments (step S35 in FIG. 6), the analysis result output unit 365 outputs to a log file 367 information indicating that a successful determination is not obtained, and additionally outputs to an erroneous analysis image file 371 the image, which does not obtain the successful determination, as an erroneous image. This erroneously analyzed image is submitted for alignment processing through human observation. As necessary, the analysis control unit 363 invokes and executes the reference mark alignment processing unit 355, the spot-by-spot alignment processing unit 357, the block-by-block alignment processing unit 359, the alignment determination unit 361, and the analysis result output unit 365; thereby a sequence of the entire analysis processing shown in FIG. 6 is implemented.

Next, an example of a screen display in the analysis processing according to this embodiment is described while referencing FIGS. 26 through 32.

Figure 26:
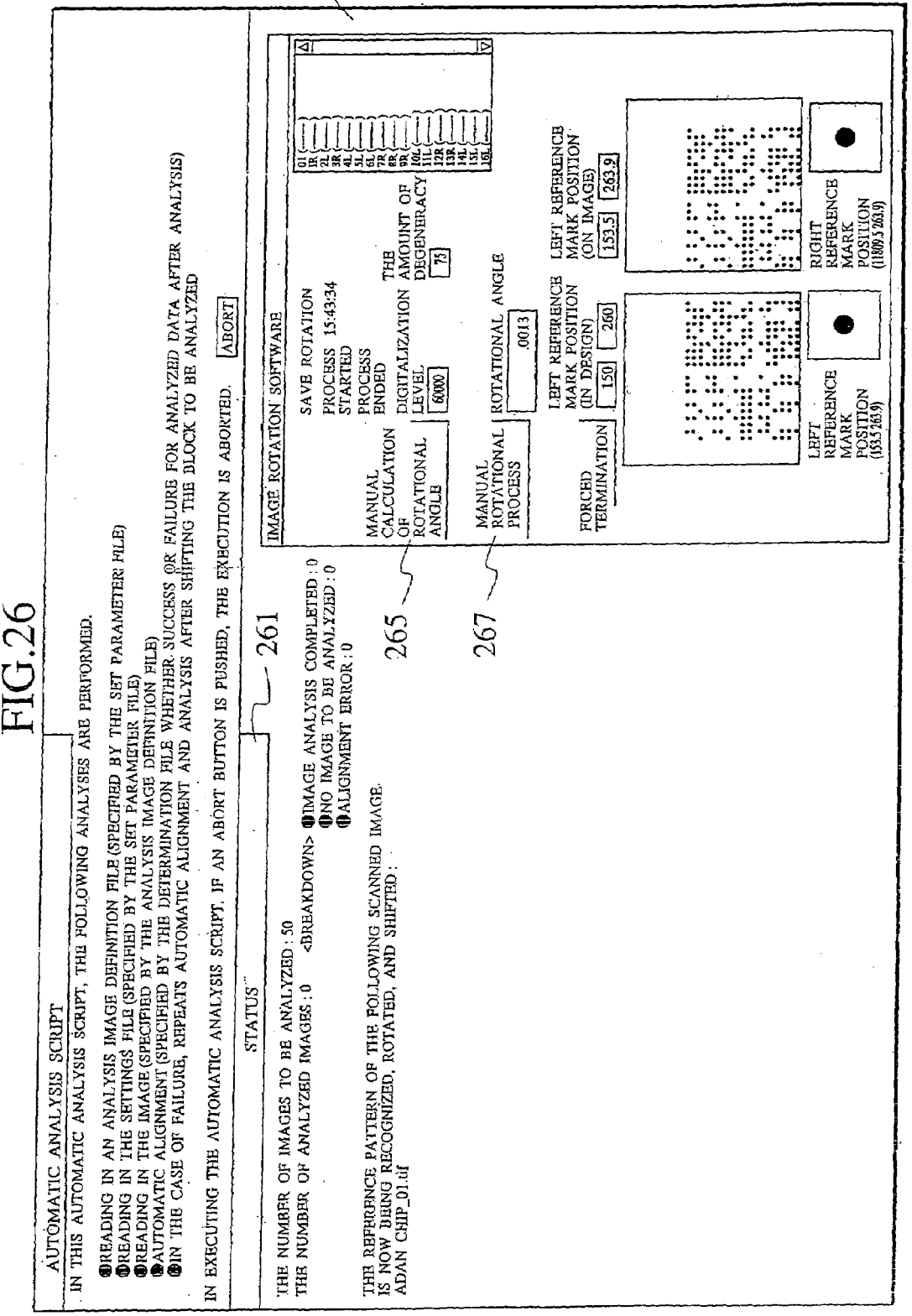
FIG. 26 is a diagram illustrating an example of an image processing screen image provided by an analysis control unit 363 according to an embodiment of the present invention.

FIG. 26 illustrates an example of a screen display during the image recognition processing of the scanned image, which is entered from the DNA microarray image file 11. As shown in a sub-window 263, the position coordinates of the reference mark, which is arranged outside of and on either side of the spot region within the scanned image, is displayed, and based on this reference mark position coordinate, a message that the rotational shift (rotational compensation) is being implemented in the recognition processing (image processing) of the scanned image is displayed. It should be noted that a manual rotation angle calculation button 265 and a manual rotation processing button 267 are provided.

FIG. 27 illustrates an example of an image display of the scanned image read in from the DNA microarray image file 11. Spots with respective fluorescent intensities including the positive controls and negative controls are arranged within the DNA microarray block.

Figure 28:
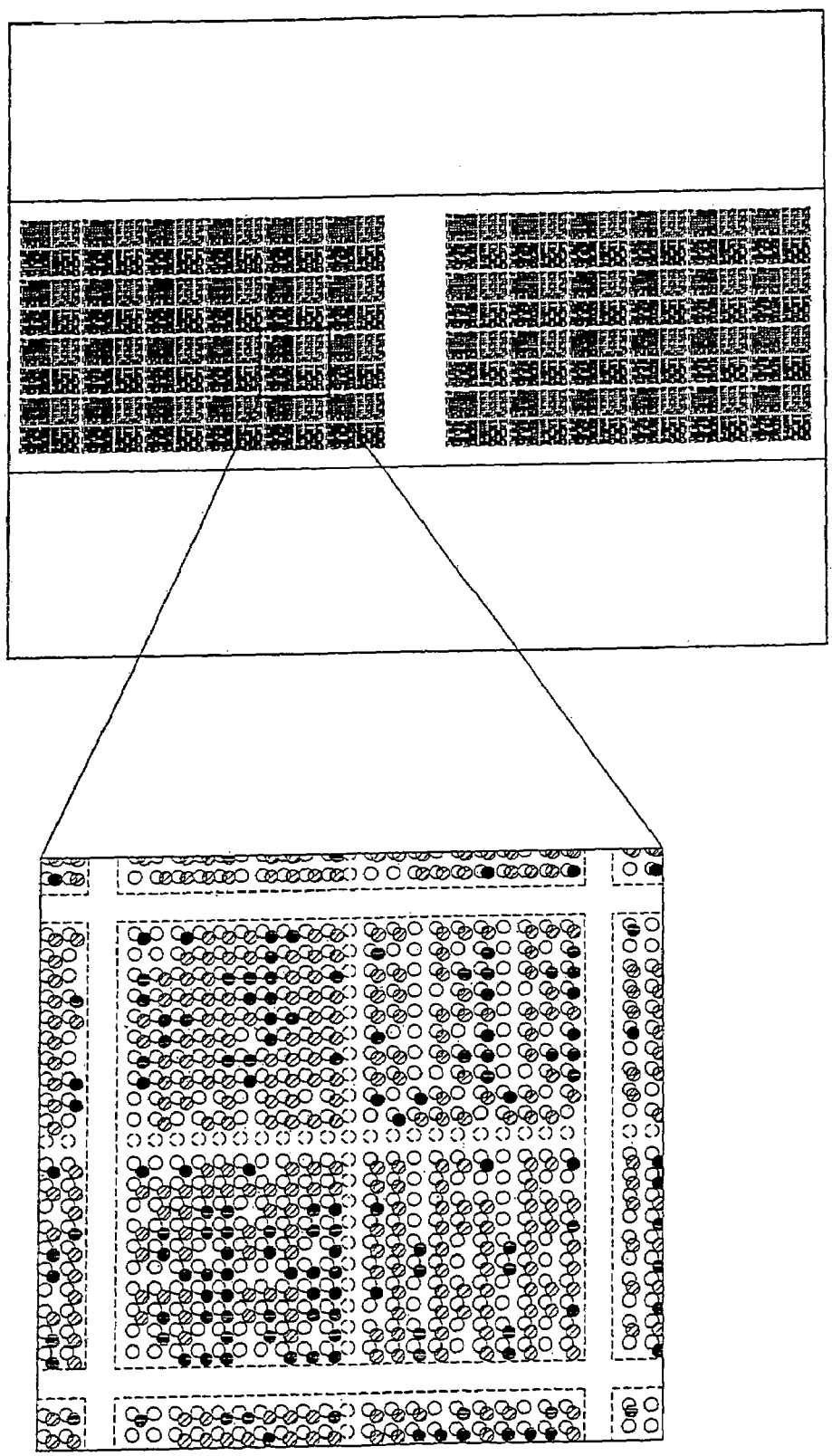
FIG. 28 is a diagram illustrating an example of the display screen image in the situation where the detection area of the template is invoked relative to the scanned image shown in FIG. 27.

FIG. 28 illustrates an example of a situation where the detection area of the template registered in the analysis parameter file 931 is invoked for the displayed representation of the image of FIG. 27. Each spot image within the DNA microarray image and each detection area on the template are misaligned.

Figure 29:
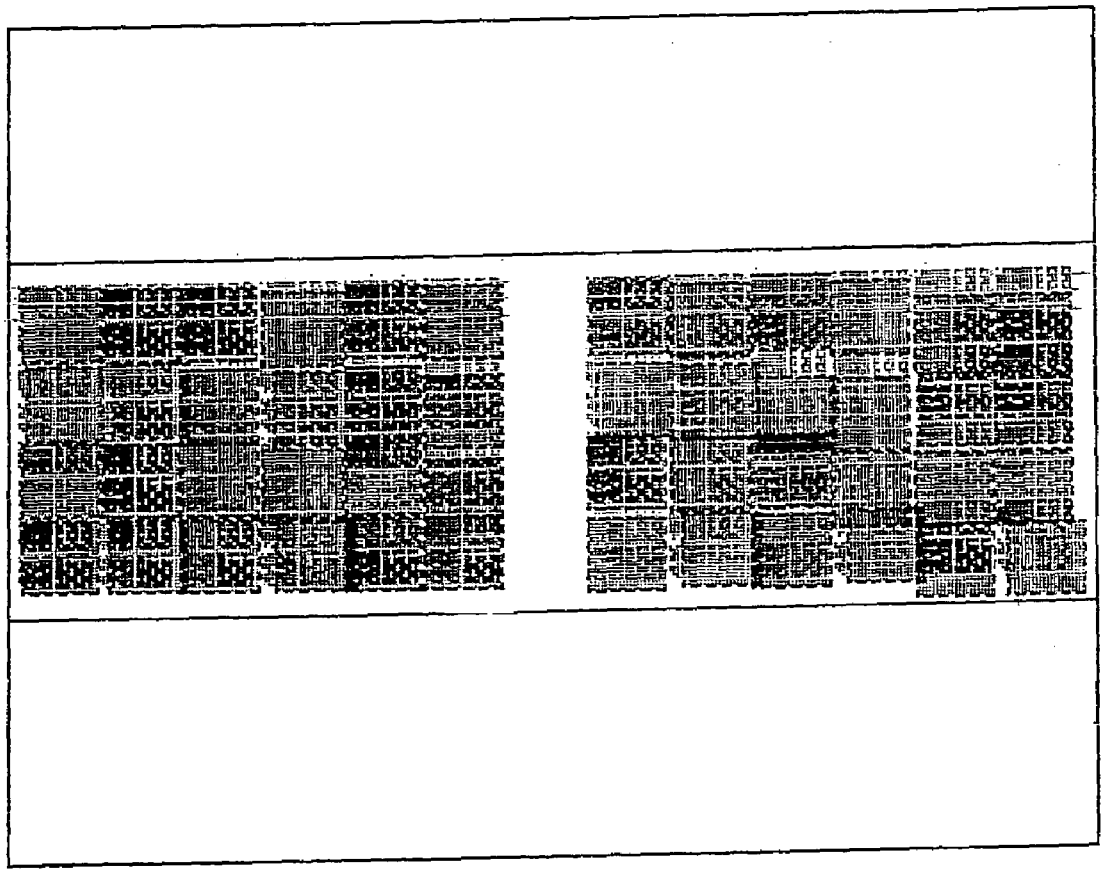
FIG. 29 is a diagram illustrating an example of a display screen image in the situation where incorrect alignment is performed without utilizing an embodiment of the present invention.

FIG. 29 illustrates an example of the post-alignment state for the image shown in FIG. 28, in the case where this embodiment is not utilized. In the case of large amounts of rotational misalignment, x direction misalignment, and y direction misalignment, the condition wherein accurate alignment is not performed, and alignment of the detection area is erroneous is illustrated. If this embodiment is not utilized, from the state in this FIG. 29, it is necessary to repeatedly performing a compensation operation, which applies to the image the detection areas by shifting them one by one through human observation.

Figure 30:
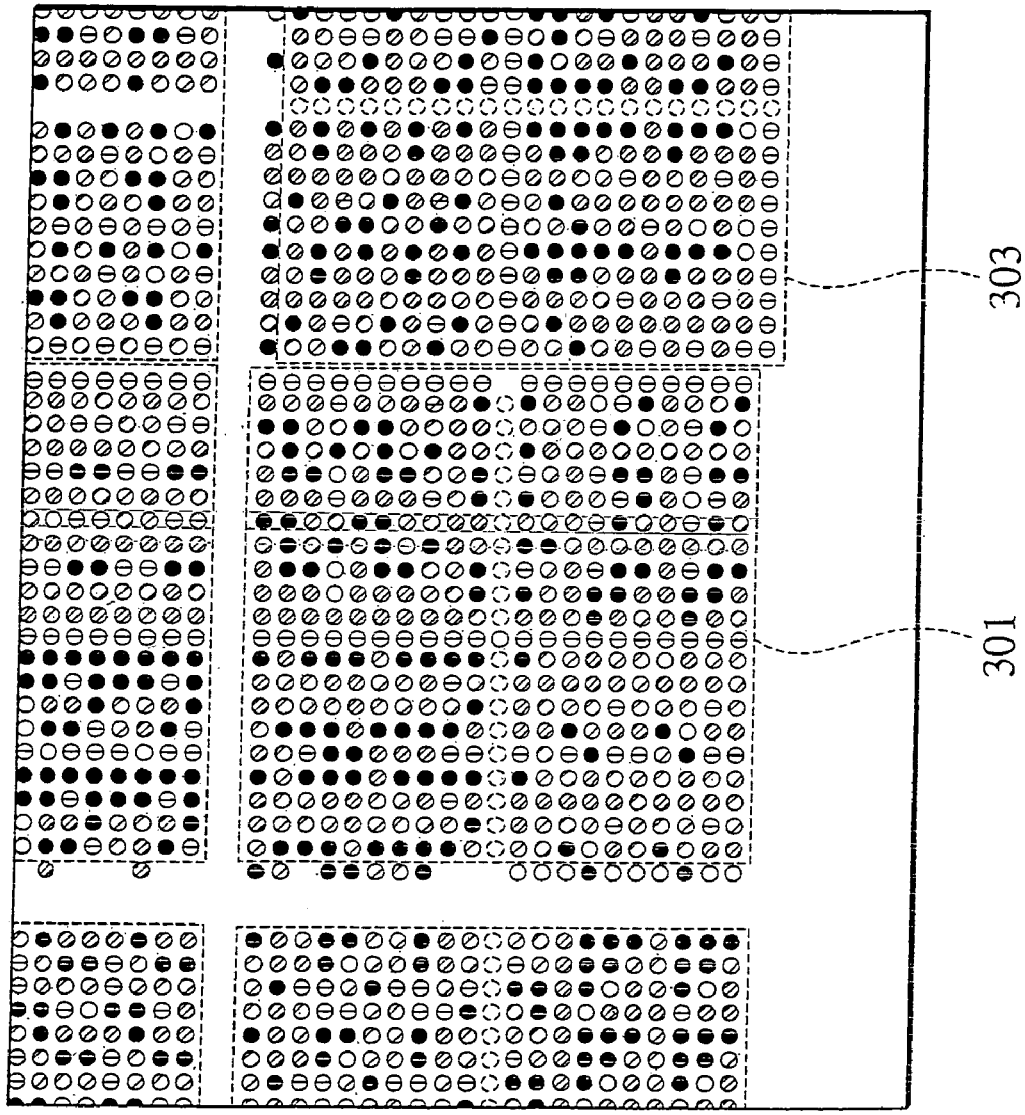
FIG. 30 is a diagram illustrating another example of a display screen image in the situation where incorrect alignment is performed without utilizing an embodiment of the present invention.

FIG. 30 illustrates an example of the post-alignment state in the case where the reference patterns comprising combinations of positive controls and negative controls in this embodiment are not utilized. Accompanying miniaturization of spot pitch upon the DNA microarrays, since spot position precision approaches the spot pitch, determination of whether each detection area is accurately applied to the respective spot merely from the position coordinate data of the detection areas becomes difficult. If this embodiment is not utilized, from the state of this FIG. 30, a person judges the overall balance by enlarging and displaying each block image to confirm whether the detection area is accurately applied.

Figure 31:
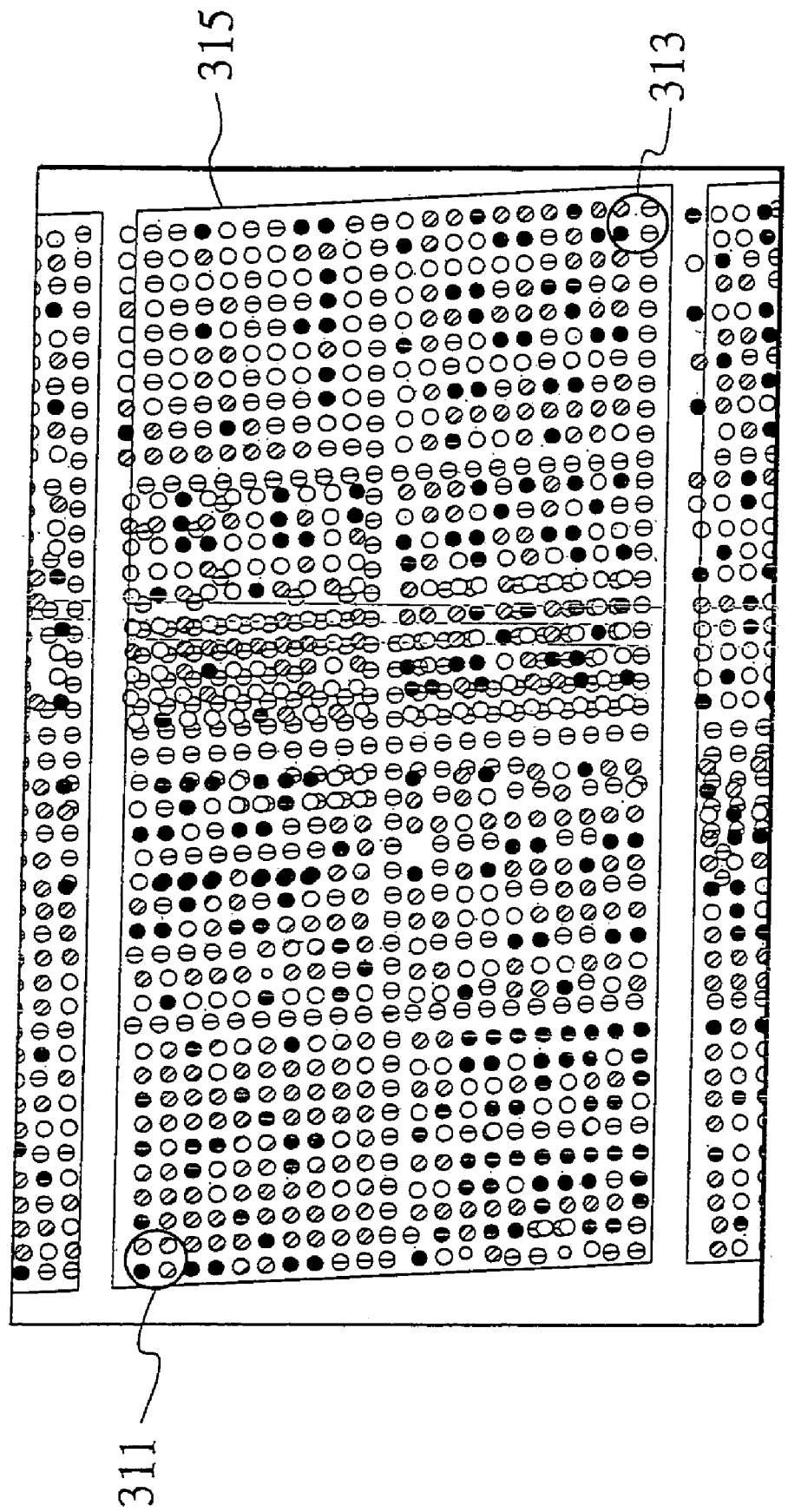
FIG. 31 is a diagram illustrating another example of a display screen image in the situation where incorrect alignment is performed without utilizing an embodiment of the present invention.

FIG. 31 illustrates an example of the situation when misalignment has occurred in the case where the reference pattern 311, which comprises a combination of positive and negative controls, is arranged in only one corner of the block. For example, if it is necessary to arrange a large block upon the DNA microarrays, rotational misalignment may easily occur, or if a reference pattern is arranged in only one corner of the block, the alignment is determined as successful in the reference determination and determination using position coordinates (block-by-block alignment) even if the alignment is erroneous. In this case, the alignment determination may be accurately performed by arranging the reference patterns comprising the positive and negative controls, for example, in an opposing corner 313.

Figure 32:
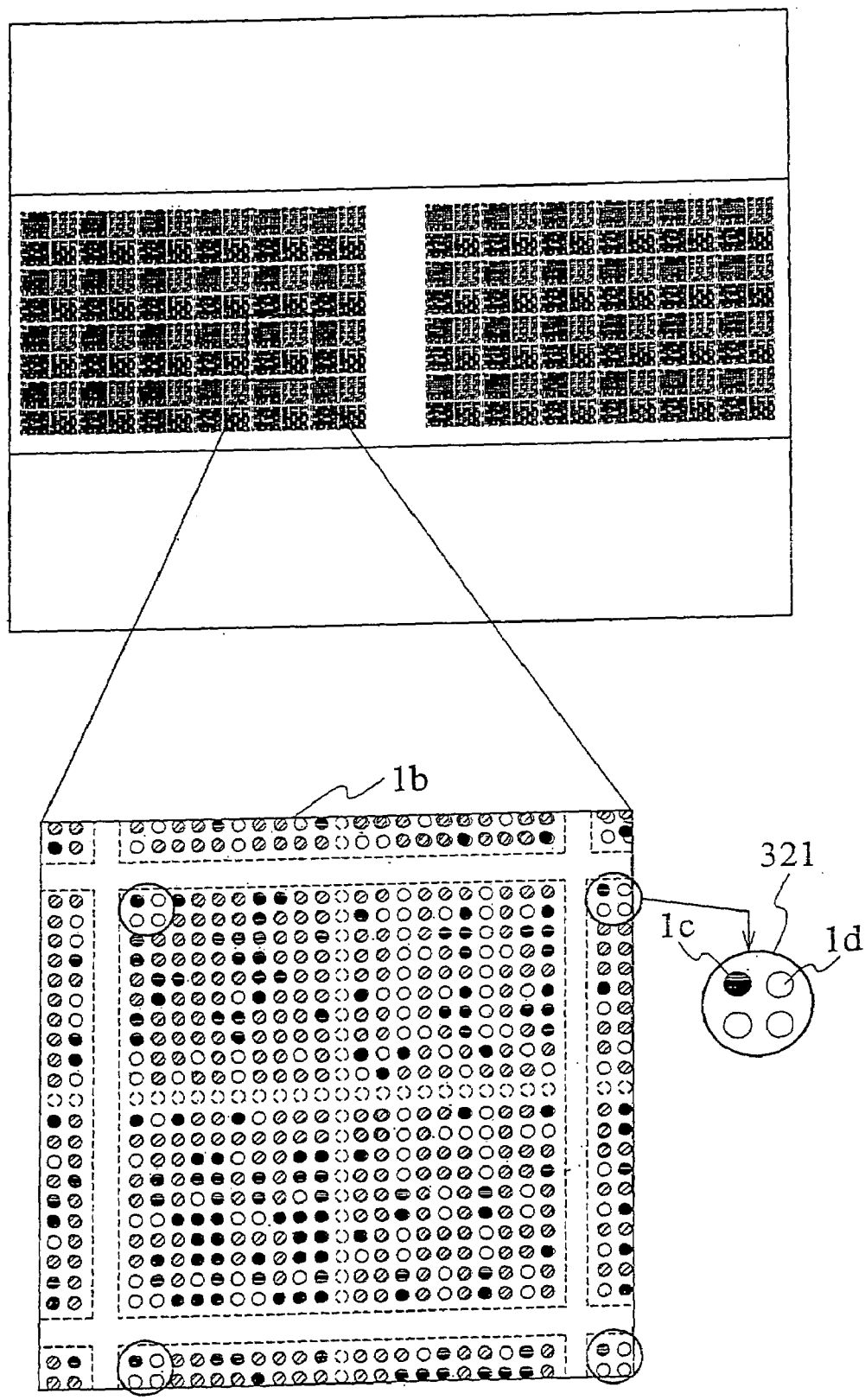
FIG. 32 is a diagram illustrating an example of a display screen image in the case where alignment determination processing provided by the analysis control unit 363 according to an embodiment of the present invention succeeds.

FIG. 32 illustrates an example of the state when the alignment determination is successful in this embodiment in the case where the reference pattern 311, which comprises a combination of positive and negative controls, is arranged in only one corner of the block. The reference pattern comprising positive and negative controls is arranged upon the block in one corner.

Figure 33:
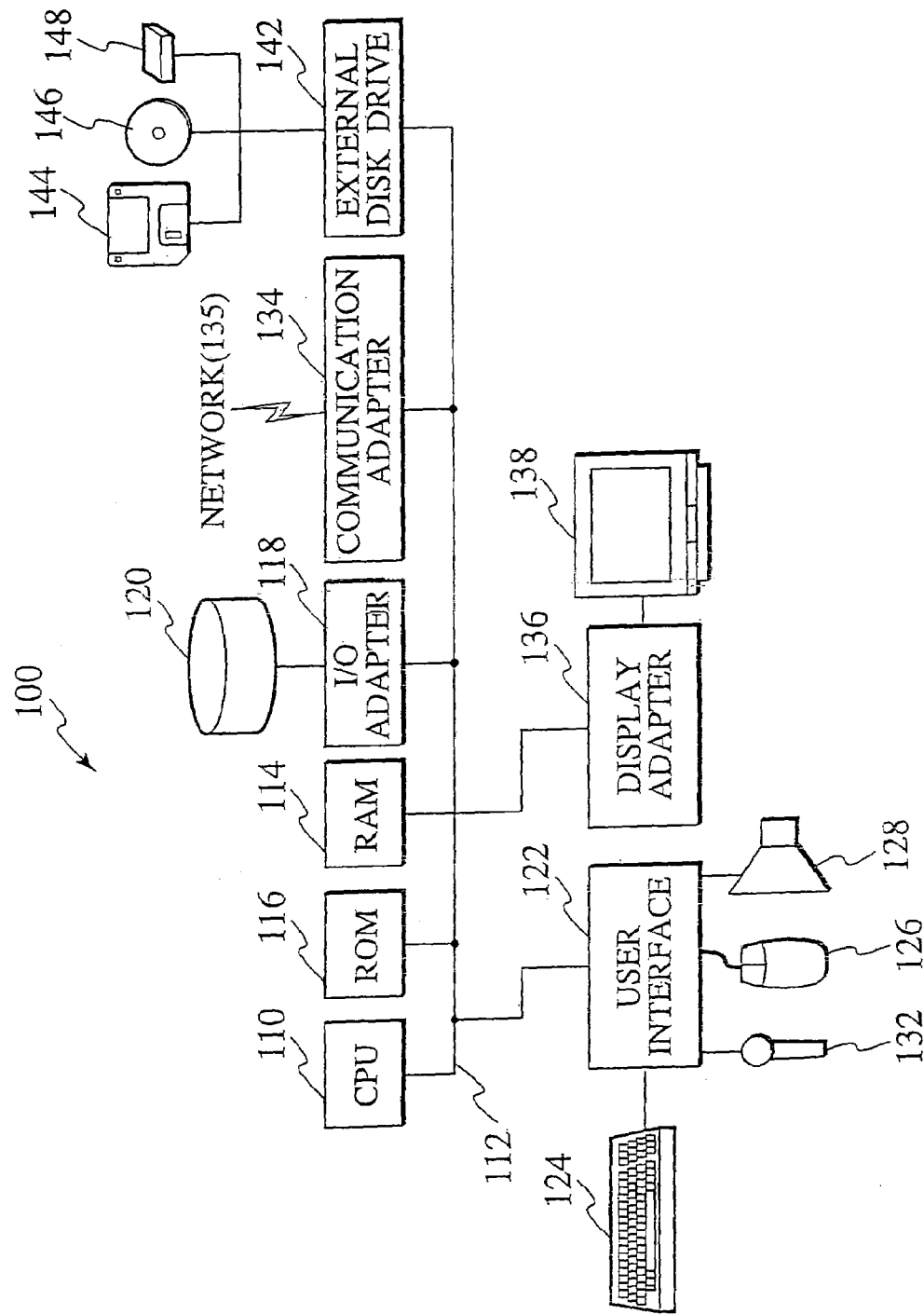
FIG. 33 is a diagram illustrating an example of the hardware structure of a control personal computer 73 and an analysis personal computer 91 according to an embodiment of the present invention.

FIG. 33 is a block diagram illustrating a hardware structure of the sample analysis apparatus and sample analysis system according to an embodiment of the present invention.

The sample analysis apparatus according to an embodiment of the present invention, for example, has a structure as shown in FIG. 33. In other words, the sample analysis apparatus according to an embodiment of the present invention is constructed by incorporating each element of the sample analysis processing within one or a plurality of computer systems.

As shown in FIG. 33, a computer system 100 comprising a central processing unit 110, such as a microprocessor, and many other units connected together through a system bus 112. This computer system comprises random access memory 114; read-only memory 116; an I/O adapter 118, which connects peripheral units, such as a hard disk unit 120, to the system bus 112; a user interface adapter 122, which connects user interface units, such as a keyboard 124, a mouse 126, a speaker 128, a microphone 132, or a touch screen (not shown in the figure) to the system bus 112; a communication adapter 134, which connects this computer system to a communication network; a display adapter 136, which connects a display unit 138 to the system bus 112; and an external disk driver 142, which respectively activates a floppy disk 144, an optical disk 146, and various memory cards 148.

It is possible to install in the computer system a sample analysis program for executing each function of the sample analysis processing according to this embodiment that is stored in these storage media, by storing the analysis program for executing each function of the sample analysis processing according to this embodiment in various computer readable storage media, which are represented by these floppy disk 144, optical disk 146, and various memory cards 148, and performing a predetermined reading operation from these storage media via the external disk driver. The sample analysis processing according to this embodiment is implemented by loading these programs into the random access memory 114 and executing thereof with the central processing unit 110. It should be noted that the above mentioned sample analysis program may be executed either on one computer or a plurality of computers linked over a network. When the program is executed on a plurality of computers, modules running on each computer are loaded therein through the storage media in which the modules are stored.

According to this embodiment, the following effects may be obtained. Namely, in the analysis of the DNA microarrays, alignment processing of the detection area to the DNA microarray image file, and alignment success/failure determination processing may be executed quantitatively, through automation, and with high accuracy. Particularly, accompanying miniaturization of spot intervals on the DNA microarrays, since manual alignment processing becomes difficult, a bottleneck due to a sequence of sample analysis processing may be widely reduced according to this embodiment.

Furthermore, parallel analysis processing becomes possible, and labor savings and expedited analysis processing may be attempted by enabling unattended consecutive execution of steps until the desired analysis data is obtained via the scanning step through analysis step.

It should be noted that in this embodiment, DNA spotted on the DNA microarrays is described by means of an embodiment, but is not limited thereto. The DNA microarrays according to this embodiment are not limited to DNA, and may be applied to, for example, biomolecules, which combine in a unique manner such as RNA and protein.

It should be fully understood that the various embodiments that are not mentioned herein are included in the present invention. Accordingly, the present invention should be limited only by the invention-specific materials related to the disclosure through the appropriate claims.

According to the present invention, during analysis of DNA microarrays, alignment processing of the detection area with an DNA microarray image file, and success/failure alignment determination processing may be executed quantitatively, through automation, and with high accuracy.

What is claimed is:

1. A probe reactive chip, comprising:
   a substrate;
   a spot region in which spots for fixing a probe capable of specifically reacting to a sample, which is marked so as to be optically detectable, are formed in a matrix on a surface of said substrate; and
   a reference pattern area, which is arranged within said spot region or approximate to said spot region, comprising a plurality of different alignment marks in order to correct a misalignment of said spots during analysis of said sample on the surface of said substrate.

2. The probe reactive chip according to claim 1, wherein said reference pattern area comprises a combination of spots that always emit light and spots that never emit light.

3. The probe reactive chip according to claim 2, wherein said spot region comprises a plurality of blocked spot sub-regions on the surface of said substrate; and
said reference pattern areas are arranged within said spot sub-regions, respectively.

4. The probe reactive chip according to claim 2, wherein said spot that always emits light within said reference pattern area is a fluorescent material emitting light at a predetermined fluorescent intensity or greater.

5. The probe reactive chip according to claim 2, wherein said spot that always emits light within said reference pattern area is a nucleic-acid binding material.

6. The probe reactive chip according to claim 2, wherein said spot that always emits light within said reference pattern area is one or more of a housekeeping gene, fragment of the housekeeping gene, or a nucleic acid including the housekeeping gene or the fragment in a base sequence thereof.

7. The probe reactive chip, according to claim 2, wherein said reference pattern area comprises a plurality of spots that never emit light being arranged surrounding a spot that always emits light.

8. The probe reactive chip according to claim 1, wherein said probe reactive chip further comprises a reference mark, which is for correcting misalignment of said spot region and which is arranged outside of said spot region on a surface of said substrate.

9. The probe reactive chip according to claim 8, wherein said reference mark is a fluorescent material emitting light at a predetermined fluorescent intensity or greater.

10. The probe reactive chip according to claim 8, wherein said reference mark is a nucleic-acid binding material.

11. The probe reactive chip according to claim 8, wherein said reference mark is one or more of a housekeeping gene, fragment of the housekeeping gene, or a nucleic acid including the house keeping gene or the fragment in a base sequence thereof.

12. The probe reactive chip according to claim 8, wherein said reference mark comprises a plurality of spots that always emit light, or a combined array of spots that always emits light and spots that never emit light.

13. The probe reactive chip according to claim 8, wherein said reference mark indicates chip inherent information including chip type and a manufactured lot identifier.

14. The probe reactive chip according to claim 1, wherein said spot region comprises a plurality of blocked spot sub-regions on the surface of said substrate; and
said reference pattern areas are arranged within said spot sub-regions, respectively.

15. The probe reactive chip according to claim 3, wherein said spot sub-regions are arranged having the interval with another adjacent spot sub-region be at least double the length of each spot interval within a spot region arranged within said spot sub-regions.

16. A sample analysis apparatus comprising:
   a reference pattern information memory unit, which defines information for a reference pattern that is formed on a probe reactive chip and that comprises a plurality of different position marks for correcting a spot misalignment;
   an image data read in unit, which reads in image data acquired by scanning a spot for fixing a probe capable of specifically reacting to a sample upon said probe reactive chip that is marked so as to be optically detectable;
   an image data alignment unit, which aligns said image data with a predefined detection target area based on reference pattern area information read from said reference pattern area information memory unit, and generates correction data for correcting misalignment of said image data and said detection target area;
   a determination unit, which determines success/failure of said alignment by analyzing image data aligned with said image data alignment unit;
   a correction unit, which correct misalignment of said image data and said detection target area based on said correction data; and
   an analysis unit, which analyzes the corrected image data, and outputs digitalized data relating to said sample.

17. The sample analysis apparatus according to claim 16, wherein said reference pattern area information stored in said reference pattern information memory unit is a pattern comprising a combination spots that always emit light and spots that never emit light.

18. The sample analysis apparatus according to claim 16, wherein said reference pattern area information stored in said reference pattern information memory unit is a relative coordinate from a reference mark.

19. The sample analysis apparatus according to claim 16, wherein said reference pattern area information stored in said reference pattern information memory unit is a relative coordinate between said reference patterns.

20. The sample analysis apparatus according to claim 16, wherein
   said reference pattern area information is defined for each of a plurality of blocked spot sub-regions on said probe reactive chip in said reference pattern information memory unit; and
   said image data alignment unit aligns said image data by said spot sub region.

21. The sample analysis apparatus according to claim 16, wherein
   said analysis unit selectively operates in either automatic mode or manual mode; and
   said determination unit repeatedly performs analysis of said aligned image data a predetermined number of times, and adds information indicating that alignment processing for the chip has failed to output data in the case where a desired analysis result cannot be obtained.

22. The sample analysis apparatus according to claim 16, further comprising
a scanning unit, which acquires said image data by scanning a spot for fixing a probe capable of specifically reacting to a sample upon said probe reactive chip that is marked so as to be optically detectable;
wherein said scanning unit and said analysis unit execute processes in parallel.

23. The sample analysis apparatus according to claim 16, wherein said image data alignment unit comprises:
a first alignment unit, which aligns a spot of said image data with a detection area by each spot in the image data; and
a second alignment unit, which aligns said image data by a plurality of blocked spot sub-regions on said probe reactive chip.

24. The sample analysis apparatus according to claim 23, further comprising
a third alignment unit, which aligns said image data by said entire spot region using a reference mark.

25. A sample analysis method comprising:
defining reference pattern area information comprising a plurality of different position marks formed on a probe reactive chip for correcting misalignment of a spot in a reference pattern information memory unit;
reading in image data acquired by scanning a spot for fixing a probe capable of specifically reacting to a sample upon said probe reactive chip and marked so as to be optically detectable;
aligning said image data to a predefined detection target area based on reference pattern area information read from said reference pattern area information memory unit and generating correction data for correcting misalignment of said image data and said detection target area;
determining whether success/failure of said alignment by analyzing said aligned image data;
correcting a misalignment of said image data and said detection target area based on said correction data; and
analyzing the corrected image data and outputting digitalized data relating to said sample.

26. The sample analysis method according to claim 25, wherein said reference pattern area information stored in said reference pattern information memory unit is a pattern comprising a combination of spots that always emit light and spot that never emit light.

27. The sample analysis method according to claim 25, wherein said reference pattern area information stored in said reference pattern information memory unit is a relative coordinate from a reference mark.

28. The sample analysis method according to claim 25, wherein said reference pattern area information stored in said reference pattern information memory unit is a relative coordinate between said reference patterns.

29. The sample analysis method according to claim 25, wherein
said reference pattern area information is defined for each of a plurality of blocked spot sub-regions on said probe reactive chip in said reference pattern information memory unit; and
said aligning of image data aligns said image data by said spot sub-regions.

30. The sample analysis method according to claim 25, wherein
said analyzing functions in either automatic mode or manual mode, selectively; and
said determining repeatedly performs analysis of said aligned image data a predetermined number of times, and adds to output data information indicating that alignment processing for the chip has failed in the case where the desired analysis result cannot be obtained.

31. The sample analysis method according to claim 25, further comprising
a scanning step for acquiring said image data by scanning a spot for fixing a probe capable of specifically reacting to a sample upon said probe reactive chip and marked so as to be optically detected;
wherein said scanning and said analyzing are performed in parallel.

32. The sample analysis method according to claim 25, wherein the image data aligning comprises:
a first alignment step for aligning a spot of said image data to a detection area by each spot in image data; and
a second alignment step for aligning said image data by a plurality of blocked spot sub-regions on said probe reactive chip.

33. The sample analysis method according to claim 32, further comprising
a third alignment step for aligning said image data by said entire spot area using a reference mark.

34. A computer-readable medium encoded with a computer program for causing a computer to execute a sample analysis process, comprising:
processing for defining in a reference pattern information memory unit information for a reference pattern area that is formed on a probe reactive chip and comprises a plurality of different position marks for correcting a spot misalignment;
processing for reading in image data acquired by scanning a spot for fixing a probe upon said probe reactive chip and capable of specifically reacting to a sample marked so as to be optically detectable;
processing for aligning said image data to a predefined detection target area based on reference pattern area information read from said reference pattern information memory unit and generating correction data for correcting misalignment of said image data and said detection target area;
processing for determining success/failure of said alignment by analyzing said aligned image data;
processing for correcting misalignment of said image data and said detection target area based on said correction data; and
processing for analyzing the corrected image data and outputting digitalized data relating to said sample.

35. The computer-readable medium according to claim 34, wherein said reference pattern area information stored in said reference pattern information memory unit is a pattern comprising a combination of spots that always emit light and spots that never emit light.

36. The computer-readable medium according to claim 34, wherein said reference pattern area information stored in said reference pattern information memory unit is a relative coordinate from a reference mark.

37. The computer-readable medium according to claim 34, wherein said reference pattern area information stored in said reference pattern information memory unit is a relative coordinate between said predefined reference patterns.

38. The computer-readable medium according to claim 34, wherein said reference pattern area information is defined for each of a plurality of blocked spot sub-regions on said probe reactive chip in said reference pattern information memory unit; and said processing for aligning image data aligns said image data by said spot sub-regions.

39. The computer-readable medium according to claim 34, wherein said analysis processing functions in either automatic mode or manual mode, selectively; and said determination processing repeatedly executes an analysis for said aligned image data for the predetermined number of times, and adds information indicating that alignment processing for the chip is failed in the case where the desired analysis result cannot be obtained to output data.

40. The computer-readable medium according to claim 34, further including scanning processing for acquiring said image data by scanning a spot for fixing a probe upon said probe reactive chip and capable of specifically reacting to a sample marked so as to be optically detectable;

wherein said scanning processing and said analysis processing are executed in parallel.

41. The computer-readable medium according to claim 34, wherein said image data alignment processing comprises:

a first alignment processing for aligning a spot of said image data to a detection area by each spot in image data; and a second alignment processing for aligning said image data by a plurality of blocked spot sub-regions on said probe reactive chip.

42. The computer-readable medium according to claim 41, further comprising a third alignment processing for aligning said image data in units of said entire spot region using a reference mark.

43. A computer-readable medium encoded with a computer program for causing a computer to execute a sample analysis process, comprising:

processing for defining in a reference pattern information memory unit information for a reference pattern area that is formed on a probe reactive chip and comprises a plurality of different position marks for correcting a spot misalignment;

processing for reading in image data acquired by scanning a spot for fixing a probe upon said probe reactive chip and capable of specifically reacting to a sample, which is marked so as to be optically detectable;

processing for aligning said image data to a predefined detection target area based on reference pattern area information read from said reference pattern area information memory unit and generating correction data for correcting misalignment of said image data and said detection target area;

processing for determining success/failure of said alignment by analyzing said aligned image data; and processing for correcting misalignment of said image data and said detection target area based on said correction data.

* * * * *

UNITED STATES PATENT AND TRADEMARK OFFICE
CERTIFICATE OF CORRECTION

| | | |
|---|---|---|
| PATENT NO. | : 7,200,254 B2 | Page 1 of 1 |
| APPLICATION NO. | : 10/235999 | |
| DATED | : April 3, 2007 | |
| INVENTOR(S) | : Shigeki Kira et al. | |

It is certified that error appears in the above-identified patent and that said Letters Patent is hereby corrected as shown below:

<u>Column 24</u>

*Line 11*: please change "3" to --14--

Signed and Sealed this

Twenty-ninth Day of May, 2007

JON W. DUDAS
*Director of the United States Patent and Trademark Office*